(12) United States Patent
Blaeser et al.

(10) Patent No.: US 8,382,796 B2
(45) Date of Patent: Feb. 26, 2013

(54) CLOSURE DEVICES, RELATED DELIVERY METHODS AND RELATED METHODS OF USE

(75) Inventors: David J. Blaeser, Champlin, MN (US); Jerome K. Grudem, Jr., Rogers, MN (US); Scott A. Olson, Zimmerman, MN (US); Mark R. Christianson, Darwin, MN (US); Scott M. Hanson, Savage, MN (US); Edward J. Anderson, Hopkins, MN (US); Patrick P. Russo, Vadnais Heights, MN (US); Dennis W. Wahr, Ann Arbor, MI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 242 days.

(21) Appl. No.: 12/626,175

(22) Filed: Nov. 25, 2009

(65) Prior Publication Data
US 2010/0069954 A1 Mar. 18, 2010

Related U.S. Application Data

(62) Division of application No. 10/411,152, filed on Apr. 11, 2003, now abandoned.

(51) Int. Cl.
*A61B 17/04* (2006.01)
(52) U.S. Cl. ........................................ 606/213
(58) Field of Classification Search ............... 606/1, 5, 606/151, 200, 213, 232, 216, 217, 218
See application file for complete search history.

(56) References Cited

U.S. PATENT DOCUMENTS

| | | | |
|---|---|---|---|
| 3,221,746 A | 12/1965 | Noble | |
| 3,402,710 A | 9/1968 | Paleschuck | |
| 3,540,431 A | 11/1970 | Mobin-Ubdin | |
| 3,620,212 A | 11/1971 | Fannon, Jr. et al. | |
| 3,638,388 A | 2/1972 | Crookston | |
| 3,638,652 A | 2/1972 | Kelley | |
| 3,657,744 A | 4/1972 | Ersek | |
| 3,844,302 A | 10/1974 | Klein | |
| 3,874,388 A * | 4/1975 | King et al. | 606/232 |

(Continued)

FOREIGN PATENT DOCUMENTS
AU 79531 3/1975
AU 670239 A 1/1994
(Continued)

OTHER PUBLICATIONS

Office Action from corresponding Japanese Application No. 2006-509750 mailed Oct. 12, 2010.

(Continued)

*Primary Examiner* — Tuan V Nguyen
(74) *Attorney, Agent, or Firm* — Lerner, David, Littenberg, Krumholz & Mentlik, LLP

(57) ABSTRACT

A device for sealing a patent foramen ovale (PFO) in the heart is provided. The device includes a left atrial anchor adapted to be placed in a left atrium of the heart, a right atrial anchor adapted to be placed in a right atrium of the heart, and an elongate member adapted to extend through the passageway and connect the left and right atrial anchors. The right atrial anchor preferably includes a plurality of arms and a cover attached to the arms. The left atrial anchor preferably also includes a plurality of arms and preferably does not include a cover. Preferably, the elongate member has a first end fixedly connected to the left atrial anchor and a portion, proximal to the first end, passing through the right atrial anchor. Preferably, the elongate member is flexible.

45 Claims, 21 Drawing Sheets

U.S. PATENT DOCUMENTS

| | | |
|---|---|---|
| 4,007,743 A | 2/1977 | Blake |
| 4,041,090 A | 8/1977 | McClure |
| 4,041,931 A | 8/1977 | Elliott et al. |
| 4,083,162 A | 4/1978 | Regan et al. |
| 4,214,587 A | 7/1980 | Sakura, Jr. |
| 4,309,776 A | 1/1982 | Berguer |
| 4,341,218 A | 7/1982 | U |
| 4,368,736 A | 1/1983 | Kaster |
| 4,485,816 A | 12/1984 | Krumme |
| 4,503,569 A | 3/1985 | Dotter |
| 4,592,754 A | 6/1986 | Gupte et al. |
| 4,603,693 A | 8/1986 | Conta et al. |
| 4,617,932 A | 10/1986 | Kornberg |
| 4,619,246 A | 10/1986 | Molgaard-Nielsen et al. |
| 4,629,451 A | 12/1986 | Winters et al. |
| 4,649,922 A | 3/1987 | Wiktor |
| 4,665,906 A | 5/1987 | Jervis |
| 4,681,588 A | 7/1987 | Ketharanathan |
| 4,710,192 A | 12/1987 | Liotta et al. |
| 4,733,665 A | 3/1988 | Palmaz |
| 4,739,762 A | 4/1988 | Palmaz |
| 4,748,982 A | 6/1988 | Horzewski et al. |
| 4,776,337 A | 10/1988 | Palmaz |
| 4,787,899 A | 11/1988 | Lazarus |
| 4,826,487 A | 5/1989 | Winter |
| 4,832,055 A | 5/1989 | Palestrant |
| 4,836,204 A | 6/1989 | Landymore et al. |
| 4,917,089 A | 4/1990 | Sideris |
| 4,921,484 A | 5/1990 | Hillstead |
| 4,994,069 A | 2/1991 | Ritchart et al. |
| 5,041,082 A | 8/1991 | Shiber |
| 5,041,090 A | 8/1991 | Scheglov et al. |
| 5,042,707 A | 8/1991 | Taheri |
| 5,052,386 A | 10/1991 | Fischer, Jr. |
| 5,064,435 A | 11/1991 | Porter |
| 5,067,489 A | 11/1991 | Lind |
| 5,067,957 A | 11/1991 | Jervis |
| 5,078,736 A | 1/1992 | Behl |
| 5,098,440 A | 3/1992 | Hillstead |
| 5,104,399 A | 4/1992 | Lazarus |
| 5,108,420 A | 4/1992 | Marks |
| 5,122,136 A | 6/1992 | Guglielmi et al. |
| 5,122,156 A | 6/1992 | Granger et al. |
| 5,135,467 A | 8/1992 | Citron |
| 5,147,370 A | 9/1992 | McNamara et al. |
| 5,171,233 A | 12/1992 | Amplatz et al. |
| 5,171,259 A | 12/1992 | Inoue |
| 5,176,692 A | 1/1993 | Wilk et al. |
| 5,190,536 A | 3/1993 | Wood et al. |
| 5,192,301 A | 3/1993 | Kamiya et al. |
| 5,207,695 A | 5/1993 | Trout, III |
| 5,211,658 A | 5/1993 | Clouse |
| 5,211,683 A | 5/1993 | Maginot |
| 5,234,447 A | 8/1993 | Kaster et al. |
| 5,234,458 A | 8/1993 | Metais |
| 5,246,445 A | 9/1993 | Yachia et al. |
| 5,254,133 A | 10/1993 | Seid |
| 5,258,000 A | 11/1993 | Gianturco |
| 5,258,042 A | 11/1993 | Mehta |
| 5,275,622 A | 1/1994 | Lazarus et al. |
| 5,284,486 A | 2/1994 | Kotula et al. |
| 5,284,488 A | 2/1994 | Sideris |
| 5,304,184 A | 4/1994 | Hathaway et al. |
| 5,304,220 A | 4/1994 | Maginot |
| 5,306,234 A | 4/1994 | Johnson |
| 5,316,023 A | 5/1994 | Palmaz et al. |
| 5,334,217 A | 8/1994 | Das |
| 5,350,398 A | 9/1994 | Pavcnik et al. |
| 5,350,399 A | 9/1994 | Erlebacher et al. |
| 5,354,309 A | 10/1994 | Schnepp-Pesch et al. |
| 5,354,336 A | 10/1994 | Kelman et al. |
| 5,360,443 A | 11/1994 | Barone et al. |
| 5,366,462 A | 11/1994 | Kaster et al. |
| 5,375,612 A | 12/1994 | Cottenceau et al. |
| 5,385,562 A | 1/1995 | Adams et al. |
| 5,387,235 A | 2/1995 | Chuter |
| 5,391,156 A | 2/1995 | Hildwein et al. |
| 5,397,345 A | 3/1995 | Lazarus |
| 5,397,355 A | 3/1995 | Marin et al. |
| 5,417,699 A | 5/1995 | Klein et al. |
| 5,425,744 A | 6/1995 | Fagan et al. |
| 5,433,497 A | 7/1995 | Koenig |
| 5,433,727 A | 7/1995 | Sideris |
| 5,443,454 A | 8/1995 | Tanabe et al. |
| 5,443,478 A | 8/1995 | Purdy |
| 5,443,497 A | 8/1995 | Venbrux |
| 5,451,235 A | 9/1995 | Lock et al. |
| 5,452,733 A | 9/1995 | Sterman et al. |
| 5,456,693 A | 10/1995 | Conston et al. |
| 5,456,712 A | 10/1995 | Maginot |
| 5,464,408 A | 11/1995 | Duc |
| 5,466,242 A | 11/1995 | Mori |
| 5,478,354 A | 12/1995 | Tovey et al. |
| 5,486,193 A | 1/1996 | Bourne et al. |
| 5,489,295 A | 2/1996 | Piplani et al. |
| 5,490,856 A | 2/1996 | Person et al. |
| 5,496,365 A | 3/1996 | Sgro |
| 5,507,769 A | 4/1996 | Marin et al. |
| 5,522,790 A | 6/1996 | Moll et al. |
| 5,522,822 A | 6/1996 | Phelps et al. |
| 5,522,836 A | 6/1996 | Palermo |
| 5,522,880 A | 6/1996 | Barone et al. |
| 5,522,882 A | 6/1996 | Gaterud et al. |
| 5,527,292 A | 6/1996 | Adams et al. |
| 5,527,322 A | 6/1996 | Klein et al. |
| 5,527,338 A | 6/1996 | Purdy |
| 5,545,214 A | 8/1996 | Stevens |
| 5,562,728 A | 10/1996 | Lazarus et al. |
| 5,597,378 A | 1/1997 | Jervis |
| 5,607,444 A | 3/1997 | Lam |
| 5,614,204 A | 3/1997 | Cochrum |
| 5,617,878 A | 4/1997 | Taheri |
| 5,618,311 A | 4/1997 | Gryskiewicz |
| 5,634,292 A | 6/1997 | Kitterman |
| 5,634,936 A | 6/1997 | Linden et al. |
| 5,645,558 A | 7/1997 | Horton |
| 5,653,747 A | 8/1997 | Dereume |
| 5,669,933 A | 9/1997 | Simon et al. |
| 5,676,670 A | 10/1997 | Kim |
| 5,681,336 A | 10/1997 | Clement et al. |
| 5,693,067 A | 12/1997 | Purdy |
| 5,693,083 A | 12/1997 | Baker et al. |
| 5,695,504 A | 12/1997 | Gifford, III et al. |
| 5,702,412 A | 12/1997 | Popov et al. |
| 5,702,421 A * | 12/1997 | Schneidt ................... 606/213 |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,735,893 A | 4/1998 | Lau et al. |
| 5,741,297 A | 4/1998 | Simon |
| 5,749,894 A | 5/1998 | Engelson |
| 5,755,778 A | 5/1998 | Kleshinski |
| 5,766,219 A | 6/1998 | Horton |
| 5,775,778 A | 7/1998 | Riley et al. |
| 5,776,097 A | 7/1998 | Massoud |
| 5,776,162 A | 7/1998 | Kleshinski |
| 5,782,860 A | 7/1998 | Epstein et al. |
| 5,797,960 A | 8/1998 | Stevens et al. |
| 5,830,228 A | 11/1998 | Knapp et al. |
| 5,833,698 A | 11/1998 | Hinchliffe et al. |
| 5,836,968 A | 11/1998 | Simon et al. |
| 5,840,064 A | 11/1998 | Liprie |
| 5,843,118 A | 12/1998 | Sepetka et al. |
| 5,843,164 A | 12/1998 | Frantzen et al. |
| 5,843,170 A | 12/1998 | Ahn |
| 5,843,175 A | 12/1998 | Frantzen |
| 5,843,176 A | 12/1998 | Weier |
| 5,846,261 A | 12/1998 | Kotula et al. |
| 5,849,005 A | 12/1998 | Garrison et al. |
| 5,853,419 A | 12/1998 | Imran |
| 5,853,422 A | 12/1998 | Huebsch et al. |
| 5,861,003 A | 1/1999 | Latson et al. |
| 5,865,791 A | 2/1999 | Whayne et al. |
| 5,868,762 A | 2/1999 | Cragg et al. |

| | | | | | | |
|---|---|---|---|---|---|---|
| 5,879,366 A | 3/1999 | Shaw et al. | | 6,652,555 B1 | 11/2003 | VanTassel et al. |
| 5,885,258 A | 3/1999 | Sachdeva et al. | | 6,652,556 B1 | 11/2003 | VanTassel et al. |
| 5,891,558 A | 4/1999 | Bell et al. | | 6,656,206 B2 | 12/2003 | Corcoran et al. |
| 5,904,680 A | 5/1999 | Kordis et al. | | 6,660,015 B1 | 12/2003 | Berg et al. |
| 5,904,703 A | 5/1999 | Gilson | | 6,682,546 B2 | 1/2004 | Amplatz |
| 5,906,207 A | 5/1999 | Shen | | 6,689,150 B1 | 2/2004 | VanTassel et al. |
| 5,910,155 A | 6/1999 | Ratcliff et al. | | 6,712,804 B2 | 3/2004 | Roue et al. |
| 5,919,200 A | 7/1999 | Stambaugh et al. | | 6,712,836 B1 | 3/2004 | Berg et al. |
| 5,921,995 A | 7/1999 | Kleshinski | | 6,776,784 B2 | 8/2004 | Ginn |
| 5,922,022 A | 7/1999 | Nash et al. | | 6,860,895 B1 * | 3/2005 | Akerfeldt et al. ............. 606/215 |
| 5,935,148 A | 8/1999 | Villar et al. | | 6,911,037 B2 | 6/2005 | Gainor et al. |
| 5,944,738 A | 8/1999 | Amplatz et al. | | 6,913,614 B2 | 7/2005 | Marino et al. |
| 5,976,159 A | 11/1999 | Bolduc et al. | | 7,338,514 B2 | 3/2008 | Wahr et al. |
| 5,976,178 A | 11/1999 | Goldsteen et al. | | 2001/0000797 A1 | 5/2001 | Mazzocchi |
| 6,013,190 A | 1/2000 | Berg et al. | | 2001/0014800 A1 | 8/2001 | Frazier et al. |
| 6,021,340 A | 2/2000 | Randolph et al. | | 2001/0021872 A1 | 9/2001 | Bailey et al. |
| 6,024,756 A | 2/2000 | Huebsch et al. | | 2001/0034537 A1 | 10/2001 | Shaw et al. |
| 6,026,814 A | 2/2000 | LaFontaine et al. | | 2001/0037129 A1 * | 11/2001 | Thill ............................ 606/213 |
| 6,035,856 A | 3/2000 | LaFontaine et al. | | 2001/0041914 A1 | 11/2001 | Frazier et al. |
| 6,036,702 A | 3/2000 | Bachinski et al. | | 2002/0022860 A1 | 2/2002 | Borillo et al. |
| 6,036,716 A | 3/2000 | Kruchinin et al. | | 2002/0026094 A1 | 2/2002 | Roth |
| 6,074,416 A | 6/2000 | Berg et al. | | 2002/0029061 A1 | 3/2002 | Amplatz et al. |
| 6,076,012 A | 6/2000 | Swanson et al. | | 2002/0035374 A1 | 3/2002 | Borillo et al. |
| 6,077,291 A * | 6/2000 | Das ............................ 606/213 | | 2002/0042625 A1 | 4/2002 | Stack et al. |
| 6,079,414 A | 6/2000 | Roth | | 2002/0068950 A1 | 6/2002 | Corcoran et al. |
| 6,080,182 A | 6/2000 | Shaw et al. | | 2002/0111647 A1 | 8/2002 | Khairkhahan et al. |
| 6,113,612 A | 9/2000 | Swanson et al. | | 2002/0123759 A1 | 9/2002 | Amplatz |
| 6,120,432 A | 9/2000 | Sullivan et al. | | 2002/0123760 A1 | 9/2002 | Amplatz |
| 6,123,715 A | 9/2000 | Amplatz | | 2002/0138094 A1 | 9/2002 | Borillo et al. |
| 6,124,523 A | 9/2000 | Banas et al. | | 2002/0138095 A1 | 9/2002 | Mazzocchi et al. |
| 6,132,438 A | 10/2000 | Fleischman et al. | | 2002/0161395 A1 | 10/2002 | Douk et al. |
| 6,152,144 A | 11/2000 | Lesh et al. | | 2002/0169474 A1 | 11/2002 | Kusleika et al. |
| 6,165,196 A | 12/2000 | Stack et al. | | 2002/0169475 A1 | 11/2002 | Gainor et al. |
| 6,168,622 B1 | 1/2001 | Mazzocchi | | 2002/0183787 A1 | 12/2002 | Wahr et al. |
| 6,171,329 B1 | 1/2001 | Shaw et al. | | 2002/0198561 A1 | 12/2002 | Amplatz |
| 6,174,322 B1 | 1/2001 | Schneidt | | 2002/0198563 A1 | 12/2002 | Gainor et al. |
| 6,193,734 B1 | 2/2001 | Bolduc et al. | | 2003/0023262 A1 | 1/2003 | Welch |
| 6,206,907 B1 | 3/2001 | Marino et al. | | 2003/0023266 A1 | 1/2003 | Borillo et al. |
| 6,210,338 B1 | 4/2001 | Afremov et al. | | 2003/0028213 A1 | 2/2003 | Thill et al. |
| 6,214,029 B1 | 4/2001 | Thill et al. | | 2003/0045901 A1 | 3/2003 | Opolski |
| 6,231,561 B1 | 5/2001 | Frazier et al. | | 2003/0057156 A1 | 3/2003 | Peterson et al. |
| 6,241,678 B1 | 6/2001 | Afremov et al. | | 2003/0120337 A1 | 6/2003 | Van Tassel et al. |
| 6,245,012 B1 | 6/2001 | Kleshinski | | 2003/0139819 A1 | 7/2003 | Beer et al. |
| 6,290,674 B1 | 9/2001 | Roue et al. | | 2003/0144694 A1 | 7/2003 | Chanduszko et al. |
| 6,325,815 B1 | 12/2001 | Kusleika et al. | | 2003/0181942 A1 | 9/2003 | Sutton et al. |
| 6,334,864 B1 | 1/2002 | Amplatz et al. | | 2003/0191495 A1 | 10/2003 | Ryan et al. |
| 6,355,052 B1 | 3/2002 | Neuss et al. | | 2003/0191526 A1 | 10/2003 | Van Tassel et al. |
| 6,368,338 B1 | 4/2002 | Konya et al. | | 2003/0195530 A1 | 10/2003 | Thill |
| 6,368,339 B1 | 4/2002 | Amplatz | | 2003/0195555 A1 | 10/2003 | Khairkhahan et al. |
| 6,371,971 B1 | 4/2002 | Tsugita et al. | | 2003/0199923 A1 | 10/2003 | Khairkhahan et al. |
| 6,379,368 B1 | 4/2002 | Corcoran et al. | | 2003/0204203 A1 | 10/2003 | Khairkhahan et al. |
| 6,391,044 B1 | 5/2002 | Yadav et al. | | 2003/0212432 A1 | 11/2003 | Khairkhahan et al. |
| 6,402,746 B1 | 6/2002 | Whayne et al. | | 2003/0225421 A1 | 12/2003 | Peavey et al. |
| 6,402,772 B1 | 6/2002 | Amplatz et al. | | 2004/0073242 A1 | 4/2004 | Chanduszko |
| 6,419,669 B1 | 7/2002 | Frazier et al. | | 2004/0092973 A1 | 5/2004 | Chanduszko et al. |
| 6,432,123 B2 | 8/2002 | Schwartz et al. | | 2004/0098047 A1 | 5/2004 | Frazier et al. |
| 6,436,088 B2 | 8/2002 | Frazier et al. | | 2004/0098121 A1 | 5/2004 | Opolski |
| 6,440,152 B1 | 8/2002 | Gainor et al. | | 2004/0133236 A1 | 7/2004 | Chanduszko |
| 6,447,531 B1 | 9/2002 | Amplatz | | 2004/0143277 A1 | 7/2004 | Marino et al. |
| 6,458,100 B2 | 10/2002 | Roue et al. | | 2004/0143291 A1 | 7/2004 | Corcoran et al. |
| 6,468,291 B2 | 10/2002 | Bates et al. | | 2004/0143293 A1 | 7/2004 | Marino et al. |
| 6,468,301 B1 | 10/2002 | Amplatz et al. | | 2004/0143294 A1 | 7/2004 | Corcoran et al. |
| D466,936 S | 12/2002 | Shaw et al. | | 2004/0162569 A1 | 8/2004 | Sikora et al. |
| 6,491,707 B2 | 12/2002 | Makower et al. | | 2004/0176799 A1 | 9/2004 | Chanduszko et al. |
| 6,506,204 B2 | 1/2003 | Mazzocchi | | 2004/0186486 A1 | 9/2004 | Roue et al. |
| 6,508,828 B1 | 1/2003 | Akerfeldt et al. | | 2004/0193147 A1 | 9/2004 | Malecki et al. |
| 6,511,496 B1 | 1/2003 | Huter et al. | | 2004/0215230 A1 | 10/2004 | Frazier et al. |
| 6,517,551 B1 | 2/2003 | Driskill | | 2004/0225324 A1 | 11/2004 | Marino et al. |
| 6,527,746 B1 | 3/2003 | Oslund et al. | | 2004/0230185 A1 | 11/2004 | Malecki et al. |
| 6,537,299 B1 | 3/2003 | Hogendijk et al. | | 2004/0267191 A1 | 12/2004 | Gifford et al. |
| 6,540,712 B1 | 4/2003 | Parodi et al. | | 2004/0267306 A1 | 12/2004 | Blaeser et al. |
| 6,551,303 B1 | 4/2003 | Van Tassel et al. | | 2005/0021016 A1 | 1/2005 | Malecki et al. |
| 6,551,344 B2 | 4/2003 | Thill | | 2005/0033327 A1 | 2/2005 | Gainor et al. |
| 6,562,058 B2 | 5/2003 | Seguin et al. | | 2005/0034735 A1 | 2/2005 | Deem et al. |
| 6,599,308 B2 | 7/2003 | Amplatz | | 2005/0038470 A1 | 2/2005 | van der Burg et al. |
| 6,616,675 B1 | 9/2003 | Evard et al. | | 2005/0043711 A1 | 2/2005 | Corcoran et al. |
| 6,623,508 B2 | 9/2003 | Shaw et al. | | 2005/0043759 A1 | 2/2005 | Chanduszko |
| 6,641,557 B1 | 11/2003 | Frazier et al. | | 2005/0059983 A1 | 3/2005 | Opolski et al. |
| 6,650,923 B1 | 11/2003 | Lesh et al. | | 2005/0065546 A1 | 3/2005 | Corcoran et al. |

| | | |
|---|---|---|
| 2005/0065547 A1 | 3/2005 | Marino et al. |
| 2005/0065548 A1 | 3/2005 | Marino et al. |
| 2005/0080406 A1 | 4/2005 | Malecki et al. |
| 2005/0090857 A1 | 4/2005 | Kusleika et al. |
| 2005/0101984 A1 | 5/2005 | Chanduszko et al. |
| 2005/0113861 A1 | 5/2005 | Corcoran et al. |
| 2005/0113868 A1 | 5/2005 | Devellian et al. |
| 2005/0119675 A1 | 6/2005 | Adams et al. |
| 2005/0131401 A1 | 6/2005 | Malecki et al. |
| 2005/0131460 A1 | 6/2005 | Gifford et al. |
| 2005/0155612 A1 | 7/2005 | Matsuura et al. |
| 2005/0267526 A1 | 12/2005 | Wahr et al. |
| 2006/0009800 A1 | 1/2006 | Christianson et al. |
| 2006/0036282 A1 | 2/2006 | Wahr et al. |
| 2007/0010852 A1 | 1/2007 | Blaeser et al. |
| 2007/0016250 A1 | 1/2007 | Blaeser et al. |
| 2007/0066994 A1 | 3/2007 | Blaeser et al. |

FOREIGN PATENT DOCUMENTS

| | | |
|---|---|---|
| CA | 2057018 | 10/1991 |
| DE | 23303 | 9/1909 |
| DE | 2822603 | 11/1979 |
| DE | 19542733 | 7/1997 |
| DE | 29713335 | 10/1997 |
| EP | 0362113 | 4/1990 |
| EP | 0539237 | 4/1993 |
| EP | 0541063 | 5/1993 |
| EP | 0637454 | 2/1995 |
| EP | 0680734 | 11/1995 |
| EP | 0684022 | 11/1995 |
| EP | 0701800 | 3/1996 |
| EP | 0712614 | 5/1996 |
| EP | 0732088 | 9/1996 |
| EP | 0732089 | 9/1996 |
| EP | 0807444 | 11/1997 |
| EP | 1013227 | 6/2000 |
| EP | 1175867 | 1/2002 |
| EP | 1281355 | 2/2003 |
| FR | 2641692 | 7/1990 |
| GB | 489316 | 7/1938 |
| GB | 2269321 | 2/1994 |
| JP | 2005-528181 T | 9/2005 |
| WO | 8908433 | 9/1989 |
| WO | 9105088 | 4/1991 |
| WO | 9300868 | 1/1993 |
| WO | 9313712 | 7/1993 |
| WO | 9320757 | 10/1993 |
| WO | 9401056 | 1/1994 |
| WO | 9521592 | 8/1995 |
| WO | 9526695 | 10/1995 |
| WO | 9528885 | 11/1995 |
| WO | 9532757 | 12/1995 |
| WO | 9601591 | 1/1996 |
| WO | 9601599 | 1/1996 |
| WO | 9614808 | 5/1996 |
| WO | 9618361 | 6/1996 |
| WO | 9622745 | 8/1996 |
| WO | 9625897 | 8/1996 |
| WO | 9640356 | 12/1996 |
| WO | 9713463 | 4/1997 |
| WO | 9713471 | 4/1997 |
| WO | 9727898 | 8/1997 |
| WO | 9741779 | 11/1997 |
| WO | 9742878 | 11/1997 |
| WO | 9801086 | 1/1998 |
| WO | 9802099 | 1/1998 |
| WO | 9803118 | 1/1998 |
| WO | 9807399 | 2/1998 |
| WO | 9808462 | 3/1998 |
| WO | 9809671 | 3/1998 |
| WO | 9816161 | 4/1998 |
| WO | 9819629 | 5/1998 |
| WO | 9819631 | 5/1998 |
| WO | 9826732 | 6/1998 |
| WO | 9827868 | 7/1998 |
| WO | 9827894 | 7/1998 |
| WO | 9838939 | 9/1998 |
| WO | 9838941 A1 | 9/1998 |
| WO | 9838942 | 9/1998 |
| WO | 9842262 | 10/1998 |
| WO | 9855027 | 12/1998 |
| WO | 9907289 | 2/1999 |
| WO | 9917816 | 4/1999 |
| WO | 9938454 | 8/1999 |
| WO | 9939646 | 8/1999 |
| WO | 9962408 | 12/1999 |
| WO | 0010452 | 3/2000 |
| WO | 0012012 | 3/2000 |
| WO | 0016705 | 3/2000 |
| WO | 0027292 | 5/2000 |
| WO | 0056245 | 9/2000 |
| WO | 0115629 | 3/2001 |
| WO | 0117435 | 3/2001 |
| WO | 0130266 | 5/2001 |
| WO | 0130267 | 5/2001 |
| WO | 0130268 | 5/2001 |
| WO | 0172367 | 10/2001 |
| WO | 0187163 | 11/2001 |
| WO | 0191844 | 12/2001 |
| WO | 0215793 | 2/2002 |
| WO | 0224106 | 3/2002 |
| WO | 02098298 | 12/2002 |
| WO | 03009880 | 2/2003 |
| WO | 03053493 | 7/2003 |
| WO | 03059152 | 7/2003 |
| WO | 03082076 | 10/2003 |
| WO | 03103476 | 12/2003 |
| WO | 2005006990 | 1/2005 |
| WO | 2005027752 | 3/2005 |
| WO | 2005039419 | 5/2005 |

OTHER PUBLICATIONS

U.U. Babic, MD, 'Experience with ASDOS for Transcatheter closure of Atrial Septal Defect and Patent Foramen Ovale,' CurentInterventional Cardlology Reports, 2:177-183, (2000).
Terry King et al., 'Secundum Atrial Sept Defect,' JAMA, vol. 235, No. 23, pp. 2506-2509, Jun. 1976.
Makram R, Ebeid, MD, "Percutaneous Catheter Closure of Secundum Atrial Sept Defects: A Review," J, Invas, Cardiol, 2002; 14: 25-31.
Brochure and instructions for Use for CardioSeal® Sept Occlusion System, An alternative FDA Approved Solution for Patients Needing Closure of Ventricular Sept Defects, NMT Med1c lnc,, 1999, pp. 1-24.
PCT Search Report of PCT/US04/010607.
U.S. Appl. No. 10/934,735, filed Sep. 7, 2004.
U.S. Appl. No. 11/522,157, filed Sep. 15, 2006.
U.S. Appl. No. 11/522,158, filed Sep. 15, 2006.
U.S. Appl. No. 11/522,193, filed Sep. 15, 2006.
U.S. Appl. No. 10/411,152, filed Apr. 11, 2003.
U.S. Appl. No. 09/870,813, filed Jun. 1, 2001.
U.S. Appl. No. 11/185,951, filed Jul. 21, 2005.
U.S. Appl. No. 11/198,325, filed Aug. 8, 2005.

* cited by examiner

CLOSURE DEVICES, RELATED DELIVERY METHODS AND RELATED METHODS OF USE

CROSS-REFERENCE TO RELATED APPLICATIONS

This application is a divisional of U.S. application Ser. No. 10/411,152, filed on Apr. 11, 2003, now abandoned, the disclosure of which is incorporated herein by reference.

FIELD OF THE INVENTION

This invention relates to devices for closing a passageway in a body, for example a patent foramen ovale in a heart, related methods and devices for delivering such closure devices, and related methods of using such closure devices for sealing the passageway.

BACKGROUND OF THE INVENTION

FIG. 1 shows a portion of a heart in longitudinal section, with the right atrium (RA), left atrium (LA), right ventricle (RV) and left ventricle (LV) shown. FIG. 1 also shows the septum primum (SP), a flap-like structure, which normally covers the foramen ovale, an opening in the septum secundum (SS) of the heart. In utero, the foramen ovale serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum secundum (SS) of a heart. A patent foramen ovale results when either partial or no fusion of the septum primum (SP) to the septum secundum (SS) occurs. In the case of partial fusion, a persistent passageway exists between the superior portion of the septum primum (SP) and septum secundum (SS). It is also possible that more than one passageway may exist between the septum primum (SP) and the septum secundum (SS).

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhaging. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of PFOs is possible with umbrella-like devices developed for percutaneous closure of atrial septal defects (ASD) (a condition where there is not a septum primum (SP)). Many of these conventional devices used for ASDs, however, are technically complex, bulky, and difficult to deploy in a precise location. In addition, such devices may be difficult or impossible to retrieve and/or reposition should initial positioning not be satisfactory. Moreover, these devices are specially designed for ASDs and therefore may not be suitable to close and seal a PFO, particularly because the septum primum (SP) overlaps the septum secundum (SS).

BRIEF SUMMARY OF THE INVENTION

In accordance with the invention, methods, tools, and devices for closing a passageway in a body, and more specifically closing a patent foramen ovale (PFO), are provided.

According to one aspect of the invention, a device for sealing a passageway in a human body is provided. The device comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and an elongate member adapted to extend through the passageway and connect the first and second anchors, the elongate member having a first end fixedly connected to one of the first and second anchors.

According to another aspect of the invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, the elongate member capable of moving through the second anchor to vary a length of the elongate member between the first and second anchors.

According to a further aspect of the invention, the device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, the second anchor including a plurality of second loop structures, and a flexible elongate member adapted to extend through the passageway and connect the first and second anchors, the elongate member capable of moving through the second anchor to vary a length of the elongate member between the first and second anchors.

According to yet another aspect of the invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein the first anchor pivots relative to the elongate member and the second anchor pivots relative to the elongate member.

According to another aspect of the present invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein each of the first and second anchors is collapsible from a deployed state to a collapsed delivery state.

According to a further aspect of the present invention, a device for sealing a passageway in a human body comprises a first anchor adapted to be placed proximate a first end of the passageway, the first anchor including a plurality of first loop structures, each loop structure including an outer loop portion and a member connecting portions of outer loop portion, a second anchor adapted to be placed proximate a second end of the passageway, and an elongate member adapted to extend through the passageway and connect the first and second anchors, the elongate member having a first end fixedly connected to the first anchor.

According to yet another aspect of the invention, an assembly for sealing a passageway in a heart is provided. The assembly comprises a guide catheter capable of extending to the passageway, and a closure device capable of sealing the passageway, the closure device including a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein the closure device is positionable within the guide catheter in a first collapsed state and extendable from the guide catheter in a second deployed state.

According to another aspect of the invention, a method of sealing a passageway in a human body is provided. The method comprises placing a first anchor proximate a first end of the passageway, the first anchor including a plurality of first loop structures, placing a second anchor proximate a second end of the passageway, and moving the second anchor relative to the first anchor along a flexible elongate member disposed between the first and second anchors within the passageway.

According to a further aspect of the invention, a method of placing a closure device to seal a passageway in a human body is provided. The method comprises advancing a catheter into a first end of the passageway and out a second end of the passageway, advancing a first anchor of a closure device out of a distal end of the catheter, withdrawing the catheter through the passageway, positioning the first anchor adjacent the second end of the passageway, advancing a second anchor of the closure device out of the distal end of the catheter, positioning the second anchor of the closure device adjacent the first end of the passageway, and advancing a lock to a position adjacent the second anchor.

According to yet another aspect of the invention, a closure device for sealing a passageway in a heart is provided. The closure device comprises a left atrial anchor configured to close a first end of the passageway, a right atrial anchor configured to close a second end of the passageway, at least one of the left atrial anchor and the right atrial anchor including a plurality of loop structures, a flexible elongate member connecting the left and right atrial anchors, wherein the elongate member has a first end fixedly connected to the left atrial anchor and wherein the right atrial anchor is movable with respect to the elongate member, and a lock configured to prevent proximal movement of the right atrial anchor relative to the flexible elongate member.

According to another aspect of the invention, a system for sealing a passage in a heart is provided. The system comprises a delivery catheter capable of extending to a position near the passage, a closure device capable of sealing the passage, the device including a first anchor adapted to be placed proximate a first end of the passage, a second anchor adapted to be placed proximate a second end of the passage, and a flexible elongate member adapted to extend through the passage and connect the first and second anchors, and a cutting tool capable of extending over the flexible elongate member to a position near the second anchor.

According to yet another aspect of the invention, a device for sealing a passageway in a human body is provided. The device comprises a first anchor adapted to be placed proximate a first end of the passageway, the first anchor including a plurality of first loop structures, each loop structure having a first end connected to the first anchor and a second free end, a second anchor adapted to be placed proximate a second end of the passageway, the second anchor including an element configured to engage a snare, and a flexible elongate member connecting the first and second anchors.

According to another aspect of the invention, a device for closing a passageway in a heart comprises a left atrial anchor adapted to be placed in a left atrium of the heart and including a plurality of uncovered arms, a right atrial anchor adapted to be placed in a right atrium of the heart and including a plurality of arms, a cover attached to the plurality of arms, and an element configured to engage a snare, and a flexible elongate member adapted to extend through the passageway and connect the left and right atrial anchors, the elongate member having a first end fixedly connected to the left atrial anchor and a second end releasably connected to the right atrial anchor.

According to yet another aspect of the invention, a device for closing a passageway in a heart comprises a left atrial anchor adapted to be placed in a left atrium of the heart and including a plurality of uncovered arms, a right atrial anchor adapted to be placed in a right atrium of the heart and including a plurality of arms and a cover attached to the plurality of arms, a flexible elongate member adapted to extend through the passageway and connect the left and right atrial anchors, the elongate member having a first end fixedly connected to the left atrial anchor, and a lock for preventing proximal movement of the right atrial anchor relative to the flexible elongate member.

According to another aspect of the invention, a device for closing a passageway in a heart comprises a left atrial anchor adapted to be placed in a left atrium of the heart and including a plurality of uncovered arms and at least one member connecting each arm to the left atrial anchor, a right atrial anchor adapted to be placed in a right atrium of the heart and including a plurality of arms and a cover attached to the plurality of arms, and a flexible elongate member adapted to extend through the passageway and connect the left and right atrial anchors, the elongate member having a first end fixedly connected to the left atrial anchor and a second end releasably connected to the right atrial anchor.

According to a further aspect of the invention, a method for retrieving a device for sealing a passageway in a heart is provided. The method comprises advancing a snare catheter through a guide catheter toward the passageway covered by a second anchor of the device, engaging a portion of the second anchor with the snare, and drawing the second anchor into the guide catheter with the snare.

According to yet another aspect of the invention, a cutting tool for severing a flexible elongate member is provided. The cutting tool comprises a cutting tool body having a distal end and a proximal end, the cutting tool body capable of extending through a guide catheter, a guide member for guiding the flexible elongate member, the guide member including a distal opening through which the flexible elongate member enters the cutting tool and a lateral opening through which the flexible elongate member exits the cutting tool, and a cutting element surrounding the guide member, wherein the cutting element is movable relative to the guide member to cut the flexible elongate member as it exits the guide member through the lateral opening of the guide member.

Additional advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference will now be made in detail to embodiments of the invention, examples of which are illustrated in the accompanying drawings. Wherever possible, the same reference numbers will be used throughout the drawings to refer to the same or like parts.

The various Figures show embodiments of patent foramen ovale (PFO) closure devices, devices and methods for delivery of the PFO closure devices, and methods of using the device to close a PFO. The devices and related methods are described herein in connection with use in sealing a PFO. These devices, however, also are suitable for closing other openings or passageways, including other such openings in the heart, for example atrial septal defects, ventricular septal defects, and patent ductus arterioses, and openings or passageways in other portions of a body such as an arteriovenous fistula. The invention therefore is not limited to use of the inventive closure devices to close PFOs.

Figure 1:
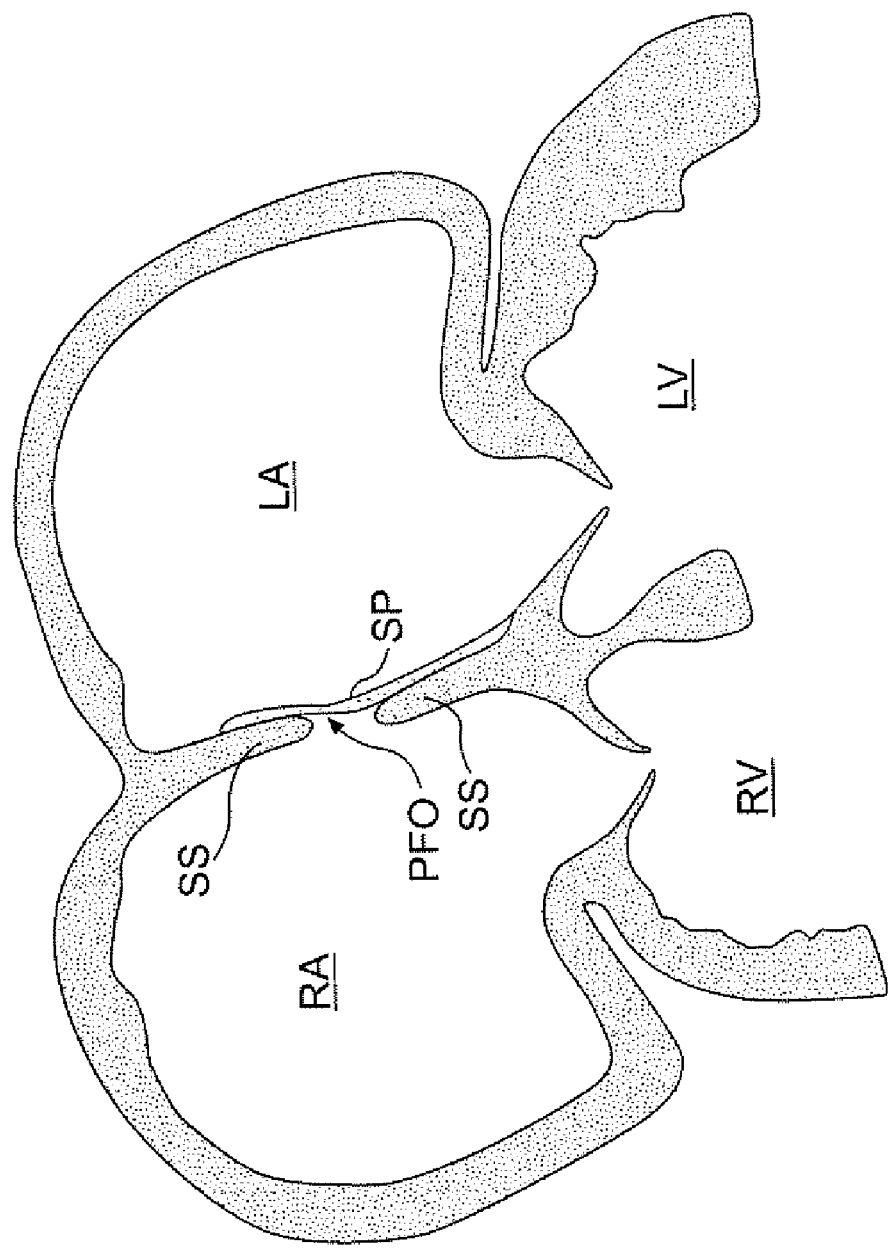
FIG. 1 is a longitudinal section of a portion of a heart having a PFO.
Figure 2:
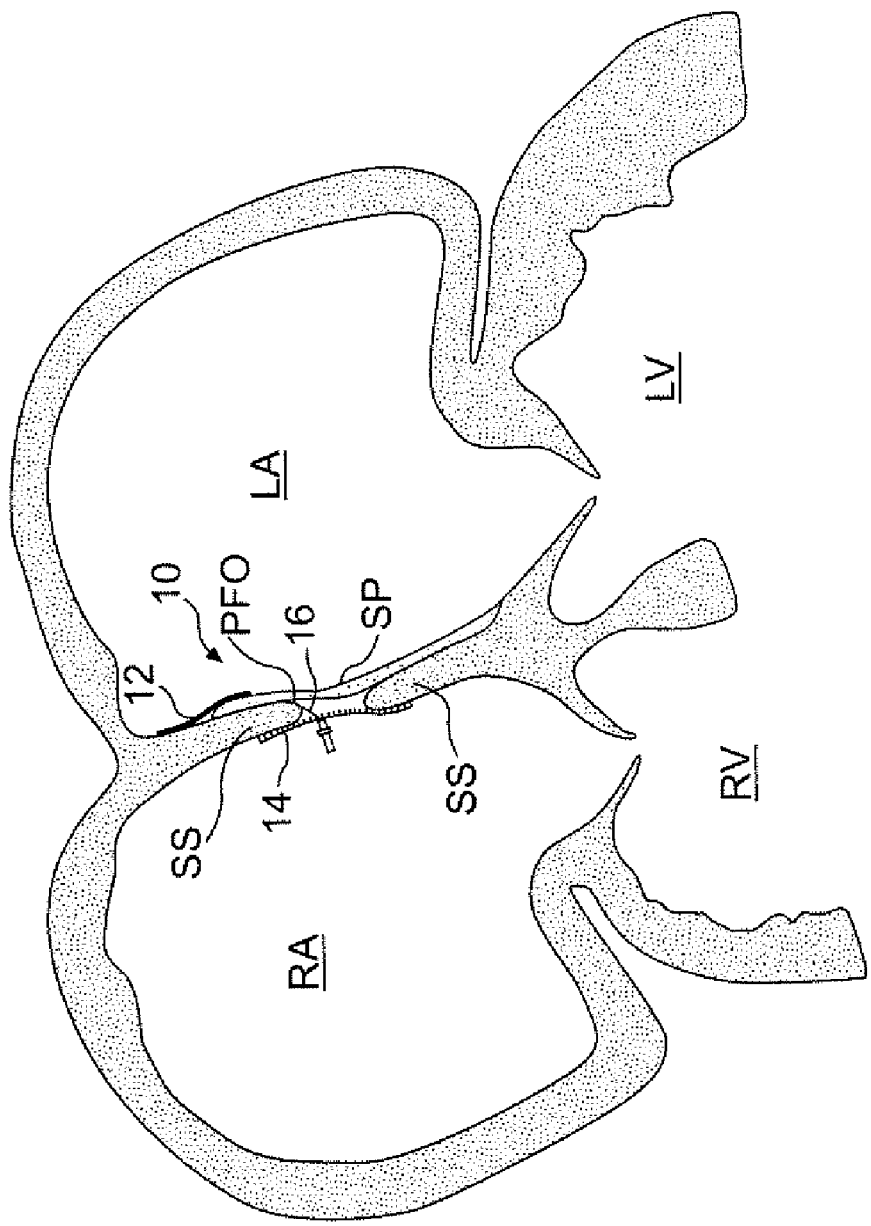
FIG. 2 is a closure device positioned in a heart to close a PFO, according to an embodiment of the present invention.
Figure 12:
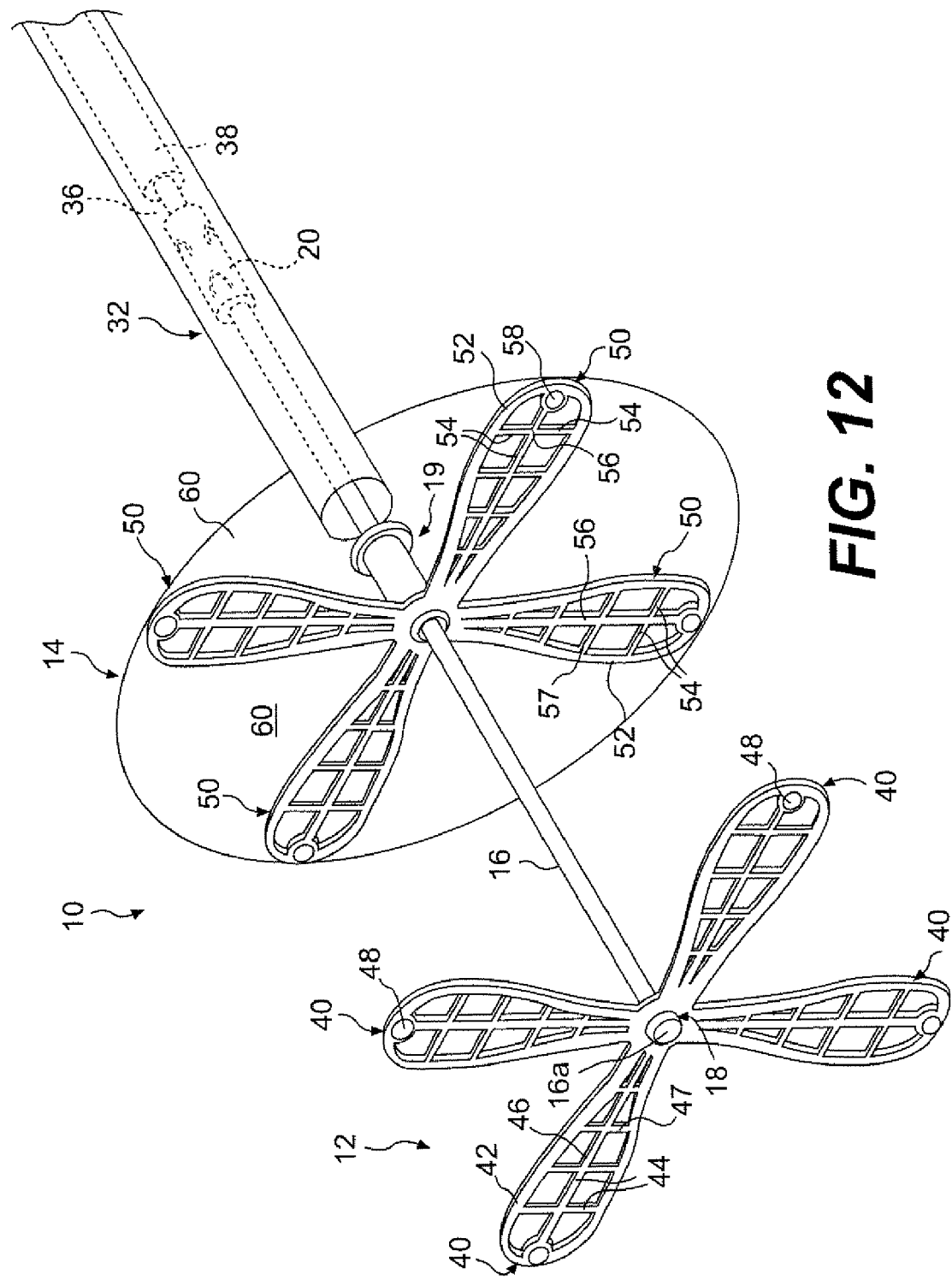
FIG. 12 is an isometric view of a closure device extending from a delivery catheter, according to one aspect of the invention.
Figure 15:
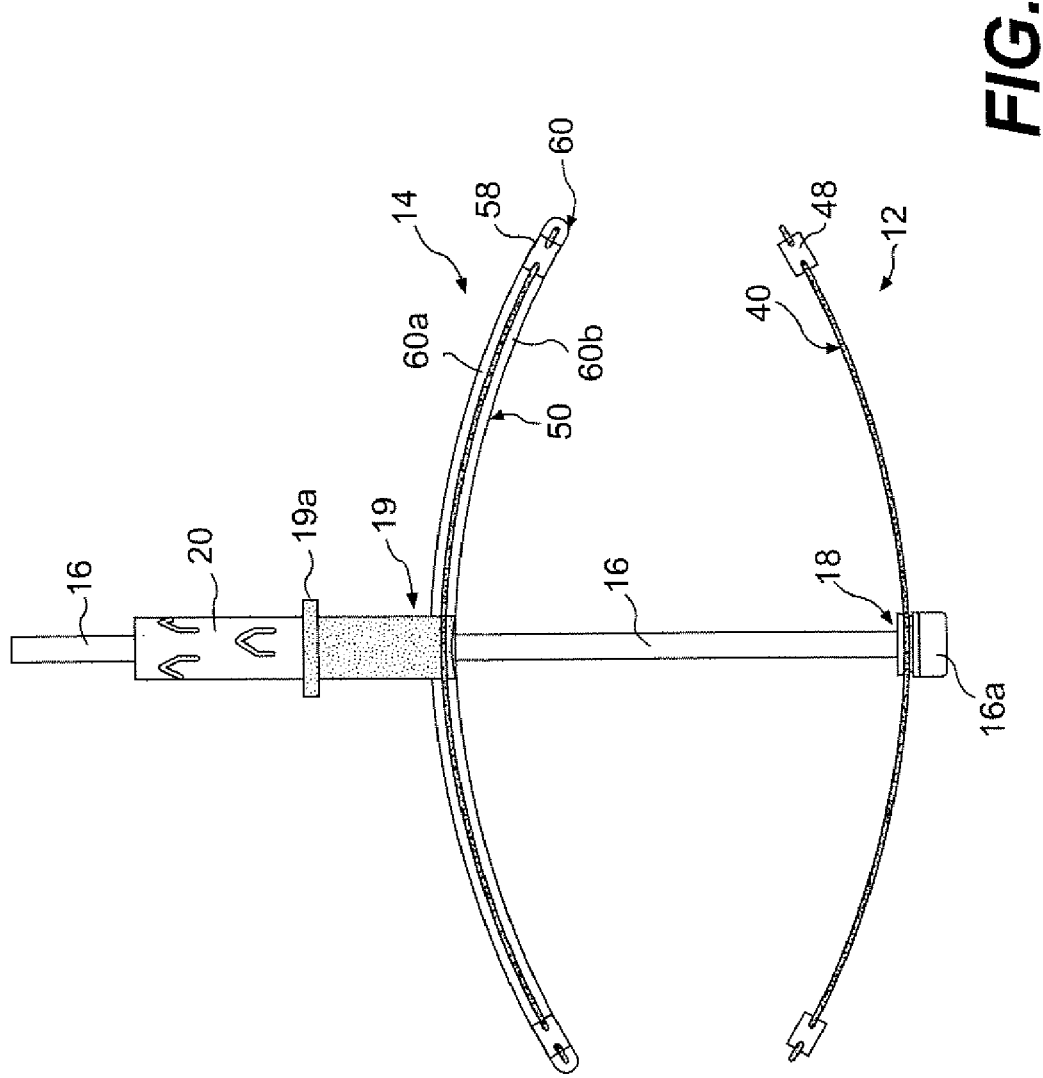
FIG. 15 is a cross-sectional side view of the closure device of FIG. 12 with a lock, according to an embodiment of the present invention.

FIGS. 2, 12, and 15 show a PFO closure device 10 according to an embodiment of the present invention. In FIG. 2, device 10 is shown positioned on either side of a PFO track (referenced as PFO in the Figures) with a portion of the device 10 passing through the PFO track, after delivery from a delivery system. The PFO track can be seen more clearly in FIG. 3, which shows a catheter disposed in the PFO track between the septum primum (SP) and septum secundum (SS). As shown in FIG. 2, closure device 10 includes a left atrial anchor 12 positioned in the LA, a right atrial anchor 14 positioned in the RA, and a tether 16 connecting the anchor structures.

As embodied herein and shown in FIGS. 2, 12, and 15, a PFO closure device 10 includes a left atrial anchor 12, a right atrial anchor 14, a tether 16, and a lock 20. FIG. 12 shows left atrial anchor 12 and right atrial anchor 14 schematically in a deployed condition. As shown in FIGS. 12 and 15, left atrial anchor 12 is permanently secured to the distal end 16a of the tether 16 via a hub 18. Hub 18 is preferably tubular in shape such that tether 16 extends through hub 18 to right atrial anchor 14. Right atrial anchor 14 is slidably disposed about the tether 16 via a second tubular hub 19. Lock 20 is advanceable along the tether 16, in a distal direction only, to secure the right atrial anchor 14 in position against the atrial tissue defining the PFO track. Tether 16 will be severed adjacent to lock 20; and left atrial anchor 12, right atrial anchor 14 connected to left atrial anchor 12 via tether 16, and lock 20 will remain in the heart to seal the PFO.

Figure 13:
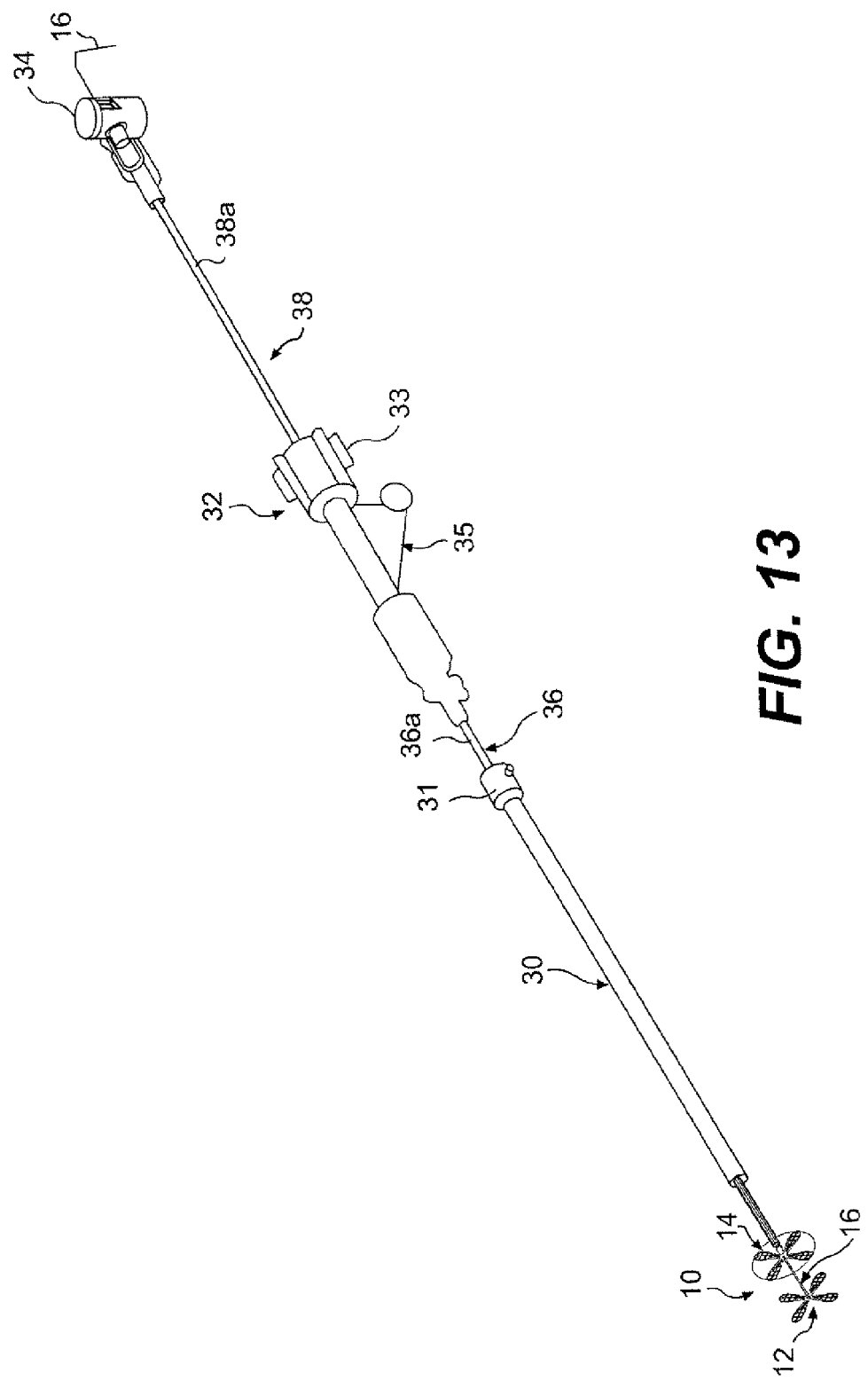
FIG. 13 is an isometric view of the closure device of FIG. 12, with a delivery catheter, and a guide catheter, according to an embodiment of the present invention.

As shown in FIG. 13, the tether 16 extends through the right atrial anchor 14, through a delivery catheter 32 (that passes through a lumen of a guide catheter 30), and emerges from the proximal end of the delivery catheter 32. An adjustable tether clip 34 provides for temporary securement of the tether 16 relative to the delivery catheter 32. The tether clip 34 may be, for example, a spring-loaded clamp similar to those used to secure laces and drawstrings on backpacks or camping and other equipment.

The tether 16 is preferably a high strength flexible polymeric material, such as a braid of polyester yarn. Preferably, such a braided yarn is approximately 0.010 to 0.025 inch in diameter, and most preferably is about 0.0175 inch. Suitable materials include, but are not limited to, multifilament yarns of ultra-high molecular weight polyethylene (UHMWPE) such as SPECTRA™ or DYNEEMA™. Other suitable materials include liquid crystal polymer (LCP) such as VECTRAN™, polyester, or other high strength fibers. Alternatively, the tether 16 could be formed of a high strength polymeric monofilament. The distal end of the tether 16 may be frayed and encapsulated with an adhesive to form a ball shape, which mechanically engages the hub 18, permanently connecting the distal end of the tether 16 to the left atrial anchor 12. Alternatively, the distal end of the tether 16 could be knotted and trimmed to yield a ball shape for engagement with hub 18 of left atrial anchor 12. FIGS. 12 and 15 illustrate an embodiment of left atrial anchor 12 and its connection to tether 16.

As embodied herein and shown in FIGS. 12 and 15, left atrial anchor 12 includes one or more arms 40, which extend radially outward from hub 18. As shown, a left atrial anchor 12 preferably includes four arms 40, although fewer or more arms may be provided. Arms 40 preferably form a unitary arm structure, such that the arms are connected to each other around hub 18. Each arm 40 is preferably ovoid in shape to prevent tissue trauma. The primary structural element of the arm 40 is a loop 42, which extends from near the center of the unitary arm structure and hub 18, towards the periphery of the left atrial anchor 12, and loops back towards the hub 18. The outer portion of the loop 42 defines an atraumatic curve. As shown in FIGS. 12 and 15, each arm 40 includes a first end connected to the hub 18 and/or other arms 40 and a second free end formed by the outer portion of the loop 42. At least the portion of each arm 40 that is unconnected to the other arms 40 of the unitary arm structure is freely movable, i.e., it is movable independently from the other arms 40.

The unitary arm structure, including the arms 40, is preferably formed from a rolled sheet of binary nickel titanium alloy (also known as nitinol). The alloy is known in the art to have superior elastic properties. The geometry of the unitary arm structure may be formed either by laser cutting or chemical etching. A smooth and passive surface is created by electropolishing. Thermal processing is used to impart a parent shape, as is known in the art. A preferred parent shape is shown in FIG. 15. This curved shape (shown in side view) for the left atrial anchor 12 presents a concave surface to the left atrial wall.

The arms 40, as shown in FIG. 12, may incorporate an optional web 44. The web 44 includes one or more radial struts 46, intersected by cross struts 47. The web 44 is preferably thinner in dimension than the loop 42. As such, the web 44 adds relatively little to the stiffness of the arm, but adds redundancy to the arm in the event of a fracture in the loop 42. Since the web 44 is thinner, any oscillating motion (primarily perpendicular to the surface of the arm) imparted to the arms 40 due to the beating of the heart will cause an oscillatory strain on the loop 42. Such a strain will be greatest near the hub 18. However, the strain imparted to the web 44 will be significantly less than that imparted to the loop 42, due to the thinness of the web 44. Thus, in the event of a fracture in the loop 42, the web 44 will maintain a connection between the arm 40 and the remainder of the unitary arm structure forming the left atrial anchor 12.

The diameter (span) of the left atrial anchor 12 is primarily determined by the size of the unitary arm structure. In a PFO closure application, the span of the unitary arm structure is preferably from about 10 mm to about 40 mm, and is most preferably from about 15 mm to about 25 mm. The preferred span width of the entire loop 42 at its widest point is preferably from about 0.050 inch to about 0.150 inch, and is most preferably about 0.100 inch. The rolled sheet that forms the loop 42 is preferably between about 0.003 inch and about 0.006 inch uniform thickness, and is most preferably about 0.045 inch, with a width of the loop 42 between about 0.002 inch and about 0.015 inch. The loop 42 is preferably wider near the hub 18, and narrower further away. The struts 46, 47 of the web 44 are thinner than the material forming the loop 42, preferably between about 0.001 inch and about 0.004 inch in width and thickness. The only structure within the left atrium is the relatively small struts of the arms 40, which are preferably well apposed to the wall tissue by virtue of their imparted parent shape. These small struts will readily be incorporated into the tissue of the left atrium, resulting in an endothelialized non-thrombogenic surface.

At the center of the unitary arm structure forming the left atrial anchor 12 is a hole, through which the hub 18 is secured. The hub 18 is preferably a tube formed of radiopaque material such as platinum alloy, and is swaged in place, forming a mechanical interlock with the unitary arm structure that forms left atrial anchor 12. The hub 18 serves to engage the distal bulb 16a of the tether 16, as previously described.

To facilitate visualization during and following implantation of the PFO closure device 10, markers 48 are provided on the arms 40. Holes near the free ends of the arms 40 are formed into the geometry of the unitary arm structure. Markers 48 may include, for example, rivets formed from a radiopaque material such as platinum alloy. The markers 48 are positioned into the holes and swaged in place.

FIGS. 12 and 15 also illustrate an embodiment of right atrial anchor 14. As embodied herein and shown in FIGS. 12 and 15, right atrial anchor 14 includes arms 50, which extend radially outward from hub 19. The structure of each arm 50 is essentially identical to that described for left atrial anchor 12. As shown in FIGS. 12 and 15, each arm 50 includes a first end connected to the hub 19 and/or other arms 50 and a second free end formed by the outer portion of the loop 52. At least the portion of each arm 50 that is unconnected to the other arms 50 of the unitary arm structure is freely movable, i.e., it is movable independently from the other arms 50. Each arm 50 is formed by a loop 52 and may include a web 54 having at least one radial strut 56 and several cross struts 57. The free end of each arm 50 may include a hole containing a marker 58.

With regard to the shape of each arm 50, thermal processing is used to impart a parent shape, as is known in the art. A preferred parent shape is shown in FIG. 15. This curved shape (shown in side view) for the right atrial anchor 14 presents a concave shape to the right atrial wall. This parent shape helps insure that the entire right atrial anchor will be apposed to atrial tissue once implanted. This apposition serves to minimize the chance for excessive thrombus formation and subsequent embolism, and also facilitates rapid incorporation of the anchor by adjacent atrial tissue.

The arms 50 form a unitary arm structure that is centered about a hub 19. Hub 19 is tubular, and is preferably formed of a radiopaque material such as platinum alloy. The inner diameter of the hub 19 is slightly larger than the diameter of the tether 16, to allow for the right atrial anchor 14 to slide relative to the tether 16. The hub 19 is secured to the unitary arm structure that forms the right atrial anchor 14 by swaging. A shoulder at the distal end of hub 19 is inserted inside the right atrial anchor 14, and flared by swaging, thus interlocking the hub 19 to the unitary arm structure, as shown in FIG. 15. The hub 19 is preferably about 0.090 inch to about 0.110 inch in length, with an enlarged ring 19a at the proximal end. This ring 19a facilitates removal or repositioning of the right atrial anchor 14 by a snare, as will be described later.

As embodied herein and shown in FIGS. 12 and 15, the right atrial anchor 14 may include a covering 60. Covering 60 provides assurance of complete closure of the PFO track, and facilitates tissue ingrowth into the right atrial anchor 14. The covering 60 preferably includes two layers, 60a, 60b, one on each side of the unitary arm structure that forms right atrial anchor 14. Alternatively, covering 60 may be a single layer attached on one side of the unitary arm structure. Preferably, the covering 60 is formed of a knitted or woven fabric of polyester, but may be formed from any suitable polymeric material such as expanded polytetrafluoroethylene. The covering 60 is secured to the unitary arm structure by suitable means, such as ultrasonically securing the two layers of fabric 60a, 60b, at their peripheries, and/or at locations between the arms 50 or within the loops 52. The covering 60 may be generally circular, as shown in FIG. 12, or any other suitable shape. The ends of arms 50 may also include small loops to receive sutures, for example, for suturing to the covering 60 of the unitary arm structure.

Figure 16:
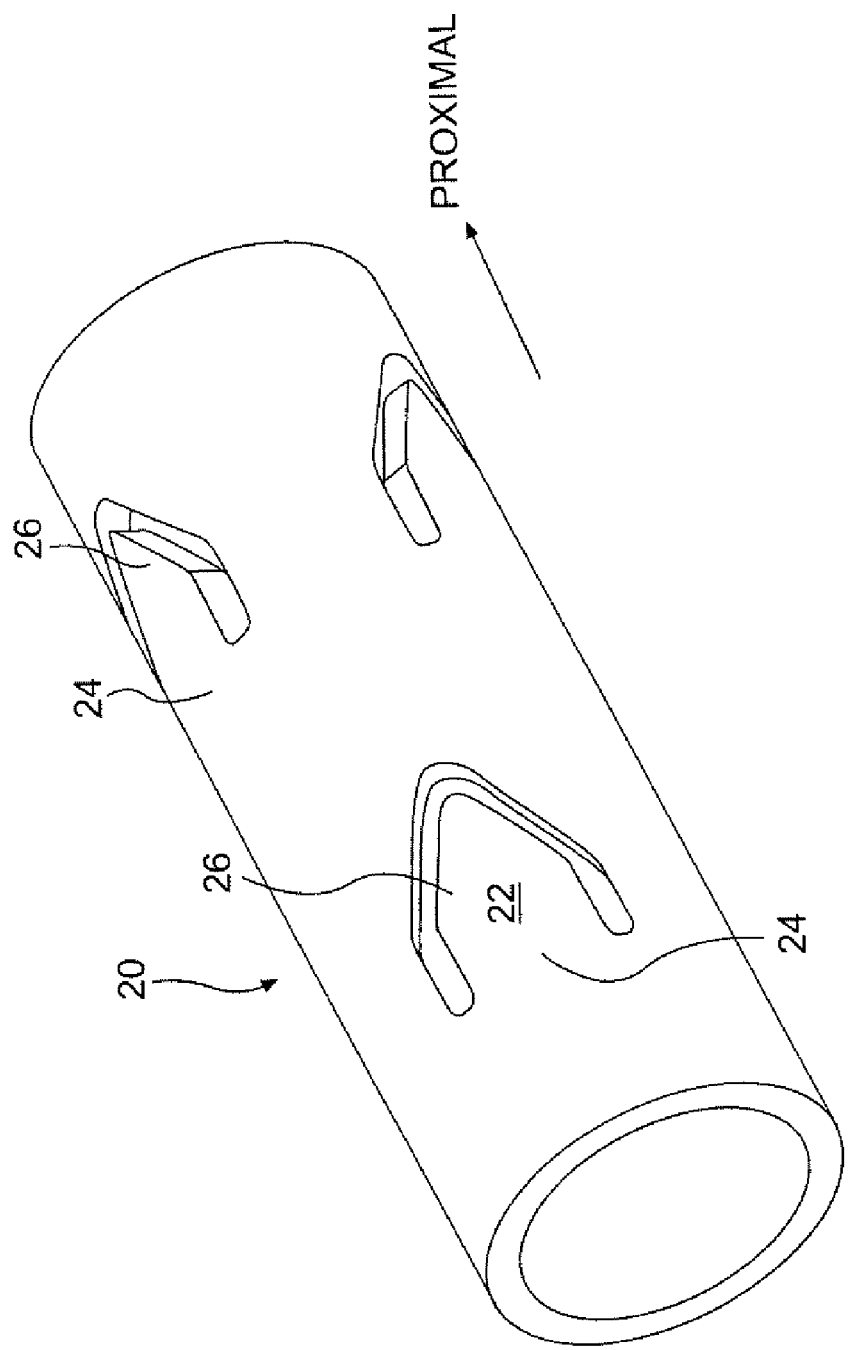
FIG. 16 is an isometric view of the lock used with the closure device in FIG. 14, according to an embodiment of the present invention.

Positioned proximally to right atrial anchor 14 on tether 16 is a lock 20. As embodied herein and shown in FIG. 16, the lock 20 is disposed about the tether 16. The lock 20 is tubular in shape and may be fabricated from a metallic material, such as a tube of nickel-titanium alloy. The inner diameter of the lock 20 is somewhat larger that the diameter of the tether 16, preferably about 0.010 inch to about 0.015 inch larger, and most preferably about 0.0125 inch larger. The lock 20 may have a wall thickness of between about 0.002 inch and about 0.005 inch, and most preferably about 0.003 inch. Lock 20 includes one or more tabs 22 formed in the tube. Preferably, lock 20 includes six tabs 22, three towards the distal end of the lock 20, and three towards the proximal end of the lock 20. The tabs towards the distal end are preferably circumferentially offset from the tabs towards the proximal end, better ensuring engagement of lock 20 with the tether 16. The tabs 22 may be formed by laser cutting. Each tab 22 includes a base 24, which connects to the main body of the lock 20, and a point 26, which serves to mechanically engage the tether 16. The tabs 22 are thermally shape set (as is known in the art) to have a parent shape with the tabs 22 deflected inward, such that the points 26 are forced to engage the tether 16. The points 26 engage the tether 16, by extending into the tether 16, when the lock 20 is moved relative to the tether 16 in one direction only. This allows the lock 20 to be advanced distally along the tether 16, while preventing proximal movement of the lock 20 along tether 16.

Figure 19:
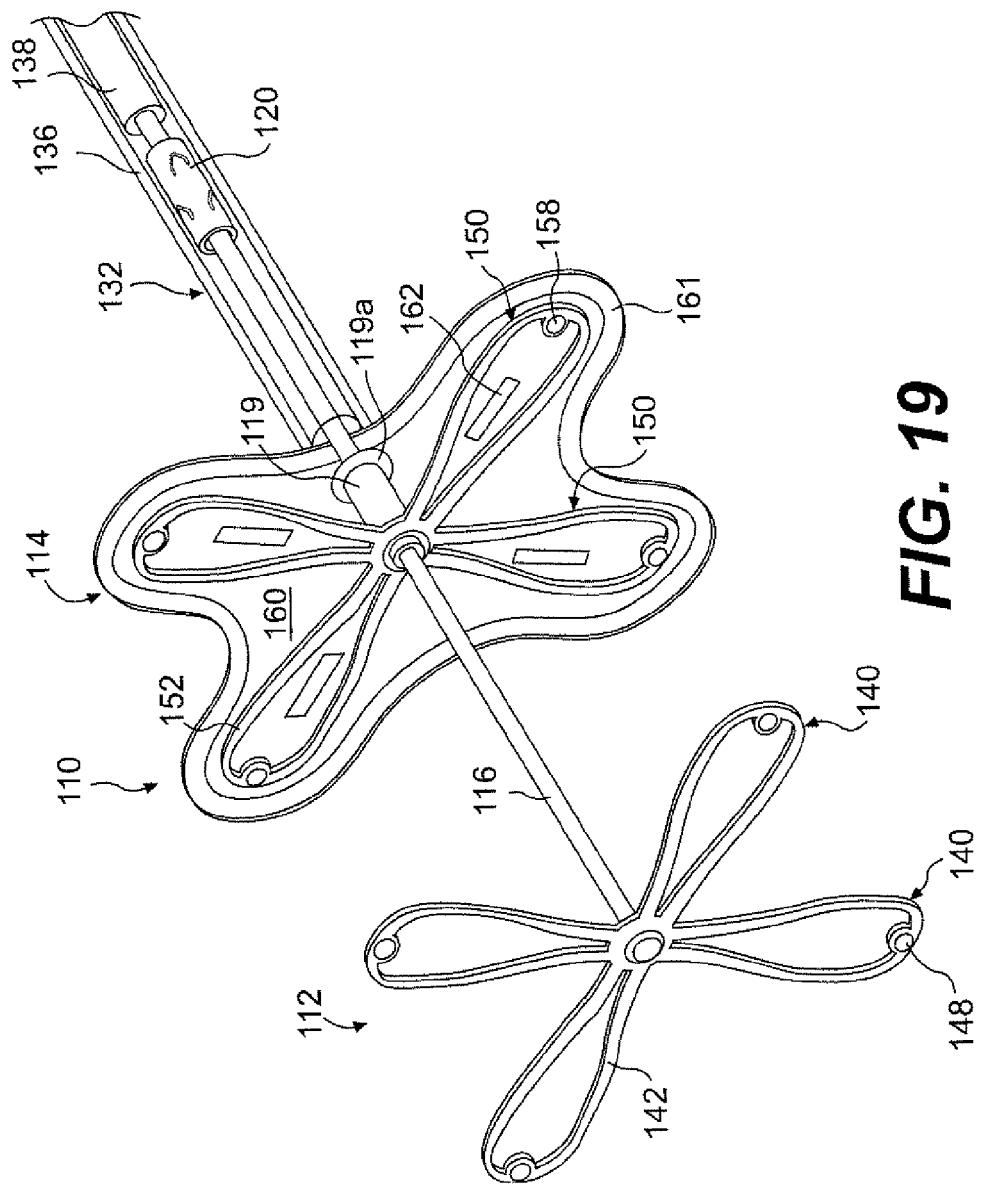
FIG. 19 is an isometric view of another embodiment of a closure device, according to the present invention.

FIG. 19 shows an alternative embodiment of a closure device 110. In at least some respects, the closure device 110 is similar to device 10 described with respect to FIGS. 12 and 15. Similar elements will be labeled with similar reference numerals in the Figure, and the differences between the embodiments will be explained. As embodied herein and shown in FIG. 19, the arms of closure device 110 may not include a web structure. Closure device 110 includes a left atrial anchor 112, a right atrial anchor 114, and a tether 116. Each anchor 112, 114, includes arms 140, 150, respectively. As shown in FIG. 19, each arm 140, 150, may be formed by a loop 142, 152, as previously described with respect to device 10. Arms 140, 150 may also include markers 148, 158, respectively, as previously described.

Additionally, the cover 160 for the right atrial anchor 114, as shown in FIG. 19, may be lobular in shape, instead of circular. Cover 160 also preferably includes two layers to effectively sandwich the arms 150. The two layers are preferably secured together at their peripheries 161 as shown, as well as at discrete locations 162 within the loops 152. The layers 160a, 160b, are secured by suitable means, such as by ultrasonic welding. The cover 160 could also be incorporated in any of the other embodiments of closure devices described in this application.

Figure 20:
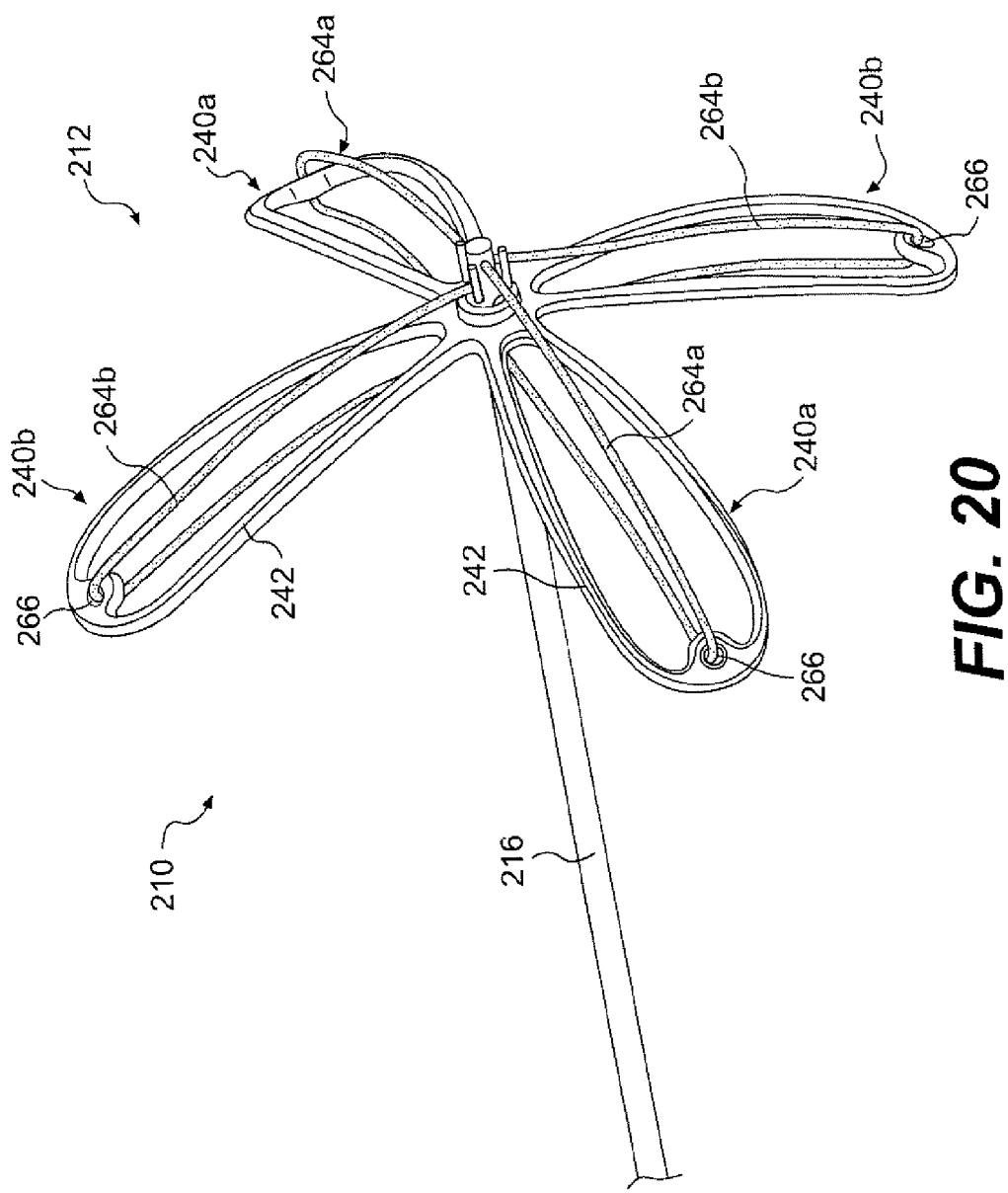
FIG. 20 is an isometric view of another alternative embodiment of a closure device, according to the present invention.
Figure 21:
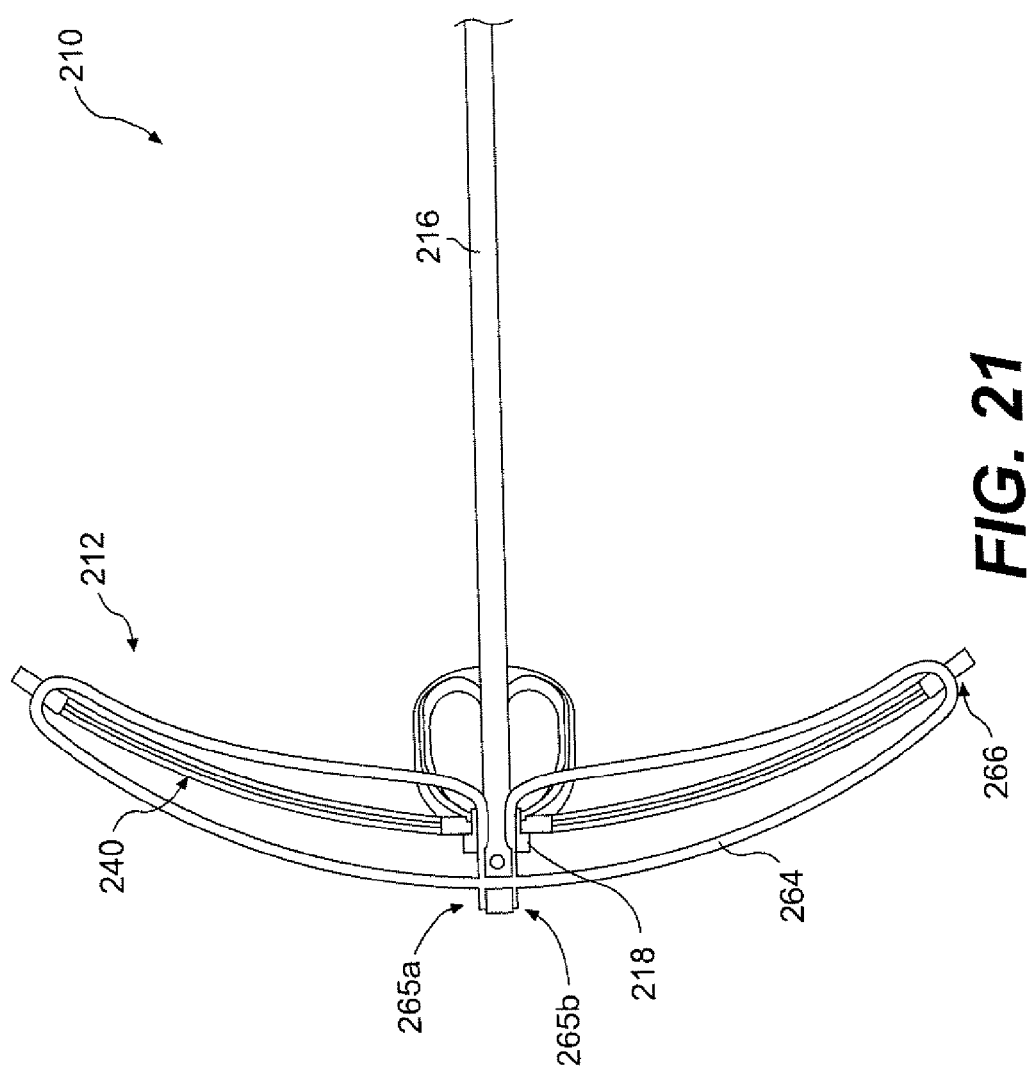
FIG. 21 is a side view of the closure device of FIG. 20.

FIGS. 20 and 21 show another alternative embodiment of a left atrial anchor 212 for a closure device 210. In at least some respects, left atrial anchor 212 is similar to left atrial anchor 112 described with respect to FIG. 19. Similar elements will be labeled with similar reference numerals in the Figures, and the differences between the embodiments will be explained. As embodied herein and shown in FIGS. 20 and 21, left atrial anchor 212 includes four arms 240. As previously discussed with respect to FIG. 19, arms 240 do not include a web structure, and are formed by loops 242. Each arm 240 may include a marker (not shown). Each left atrial arm 240 may further include a structure to prevent embolism of that arm 240, in the event of arm fracture. This structure performs a function similar to that the web 44, shown in FIG. 12, performs.

As shown in FIGS. 20 and 21, one or more safety lines 264 extend parallel to the arms 240 of the left atrial anchor 212. Two safety lines 264a, 264b are shown in FIG. 20. A first safety line 264a secures two arms 240a of the anchor 212, and a second safety line 264b secures the remaining arms 240b. Each safety line 264a, 264b is preferably formed of a flexible but strong polymeric material, such as a braided filament bundle of polyester or ultra-high molecular weight polyethylene. The safety lines 264 preferably pass through the ends of the arms 240 through holes 266. Although not shown, additional holes may be provided near the ends of the arms to contain markers, as described above. The preferred path for each safety line 264 is shown in FIG. 21. The two ends 265a, 265b of the safety line 264 lie next to the distal end of the tether 216. The safety line 264 extends through the hub 218, then along and parallel to two arms 240, through the holes 266, back along and parallel to the two arms 240, and then through the body of the tether 216 itself at a very distal end.

Alternatively, each arm 240 may include a separate safety line 264. For example, the end 265 of the line 264 could be adjacent the end of the tether 216 as described above, extend through the hub 218 and parallel to the arm 240 to the hole 266, and terminate in a knot or encapsulated fray at a hole (not shown) in the end of the tether 216, as previously described in connection with the distal end of the tether 216.

Figure 17:
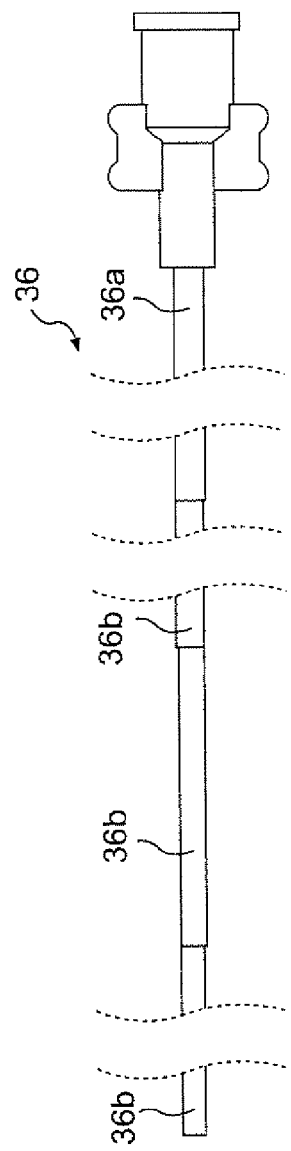
FIG. 17 is a side view of an outer tube of the delivery catheter, according to an embodiment of the present invention.
Figure 18:
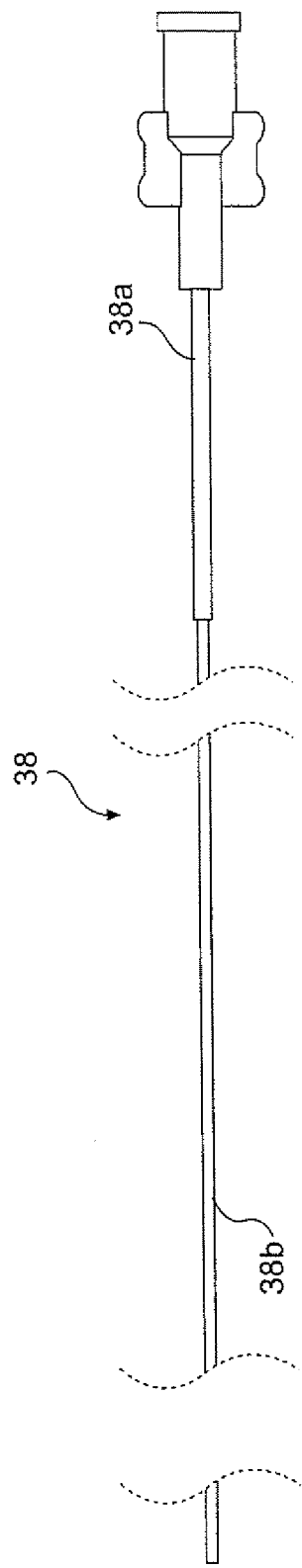
FIG. 18 is a side view of an inner tube of the delivery catheter, according to an embodiment of the present invention.

FIG. 13 shows the closure device 10 positioned relative to an embodiment of a delivery catheter 32. As embodied herein and shown in FIGS. 12, 13, 17, and 18, the delivery catheter 32 includes an outer tube 36 and an inner tube 38. The outer tube 36 may be formed from a polymer, preferably high density polyethylene. The distal portion 36b of the outer tube 36 preferably has an inner diameter of between about 0.040 inch and about 0.060 inch, and is most preferably about 0.048 inch, with a wall thickness of between about 0.005 and about 0.010 inch, and most preferably about 0.008 inch. As shown in FIG. 17, the distal portion 36b of the outer tube 36 may taper along its length to the most distal end. Alternatively, the distal portion 36b of the outer tube may have a constant inner and outer diameter. The proximal portion of the outer tube 36 preferably has an inner diameter of between about 0.050 inch and about 0.070 inch, and is most preferably about 0.060 inch, with a wall thickness of between about 0.005 inch and about 0.010 inch, and most preferably about 0.007 inch. The dimensions of the outer tube 36 are such that it can engage and abut with the hub 19 of the right atrial anchor 14 during the delivery of the device 10. The proximal end of the outer tube 36 includes a rigid sleeve 36a, formed of a hypotube which surrounds the polymeric tube. The rigid sleeve 36a serves to prevent kinking of the outer tube 36 during the delivery of the device. The length of the proximal rigid sleeve 36a is preferably between about 10 cm and about 20 cm, and is most preferably about 14 cm. The length of the outer tube 36, including the rigid sleeve 36a, is preferably between about 100 cm and about 130 cm, and is most preferably about 115 cm.

The inner tube 38 of delivery catheter 32 may be formed from a suitable polymer, such as PEBAX 6333™, and have a preferred inner diameter of between about 0.020 inch and about 0.040 inch, most preferably about 0.030 inch, with a wall thickness of between about 0.003 inch and about 0.010 inch, and most preferably about 0.006 inch. The preferred dimensions of the inner tube 38 are such that it can engage and advance the lock 20 along the tether 16. The distal end 38b of the inner tube 38 preferably has a uniform inner and outer diameter. The proximal end of the inner tube 38 also includes a rigid sleeve 38a, formed of a hypotube surrounding the polymeric tube. The length of the rigid sleeve 38a is preferably between about 15 cm and about 30 cm, and is most preferably about 23 cm. The length of the inner tube 38, including the rigid sleeve 38a, is preferably between about 90 cm and about 110 cm, and is most preferably about 100 cm.

In FIGS. 12 and 13, left atrial anchor 12 and right atrial anchor 14 are shown deployed from delivery catheter 32. As shown in FIG. 13, delivery catheter 32 may be used with a guide catheter 30. Although not shown, guide catheter 30 may have a pre-formed curve near its distal end. Guide catheter 30 can be any suitable, conventional guide catheter. A suitable, exemplary guide catheter is known as "Mullins" guide catheter, sold commercially by Cook. Connected to the proximal end of guide catheter 30 is a hemostasis valve 31.

Prior to deployment of closure device 10, guide catheter 30 would be delivered by conventional techniques to the site of the PFO. Such conventional techniques may include the temporary use of a guide wire (not shown).

Figure 14:
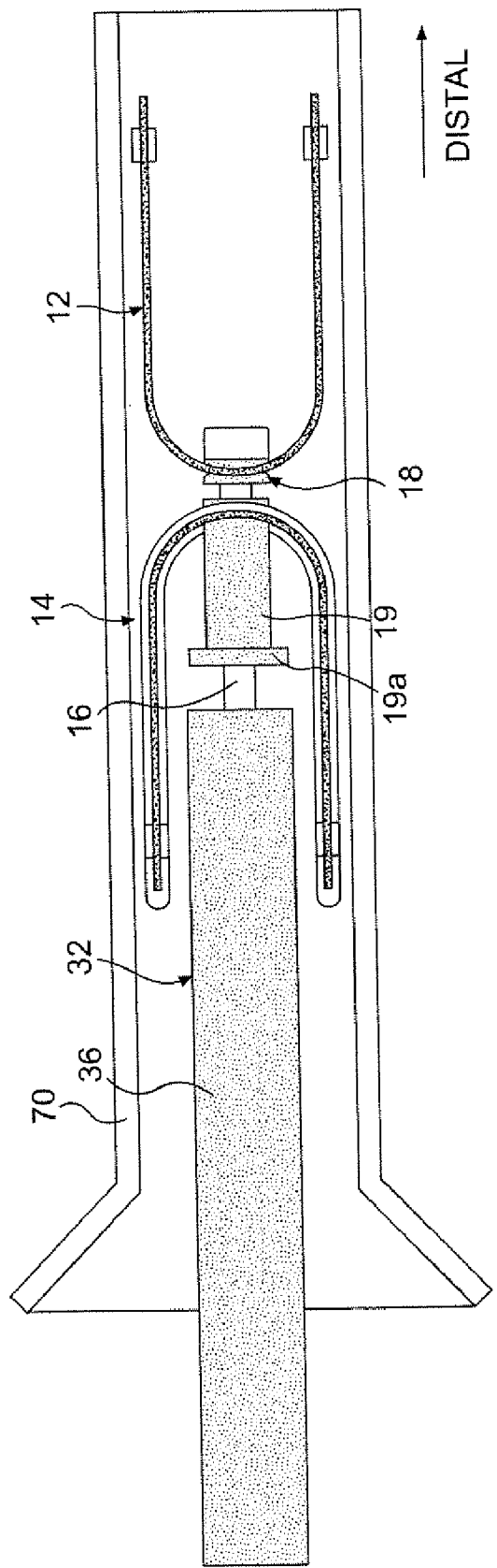
FIG. 14 is a cross sectional side view of a closure device and a delivery catheter positioned in a loading tube prior to introduction into a guide catheter, according to an embodiment of the present invention.

FIG. 14 illustrates the closure device 10 in a collapsed condition prior to delivery, within a loading tube 70. As shown in FIG. 14, loading tube 70 preferably has a flared proximal end to facilitate introduction of the device 10 and delivery catheter 32 into the loading tube 70. This is the state of the closure device 10 and delivery catheter 32 prior to introduction into the previously placed guide catheter 30. As shown in FIG. 14, the outer tube 36 of the delivery catheter 32 has a size that will abut the hub 19 of right atrial anchor 14 as tube 36 moves along tether 16. The right atrial anchor 14 also may move along tether 16 to abut the left atrial anchor 12. This abutment allows the left and right atrial anchors 12, 14 to move in response to movement of the delivery catheter 32 within the guide catheter 30. The condition in which the structures abut one another may be created and maintained by having the tether clip 34 positioned against the proximal end of the delivery catheter 32, after removing any initial slack in the tether 16. As shown in FIG. 14, the arms 40 of the left atrial anchor 12 are collapsed in the distal direction, while the arms 50 of the right atrial anchor 14 are collapsed in a proximal direction.

Figure 3:
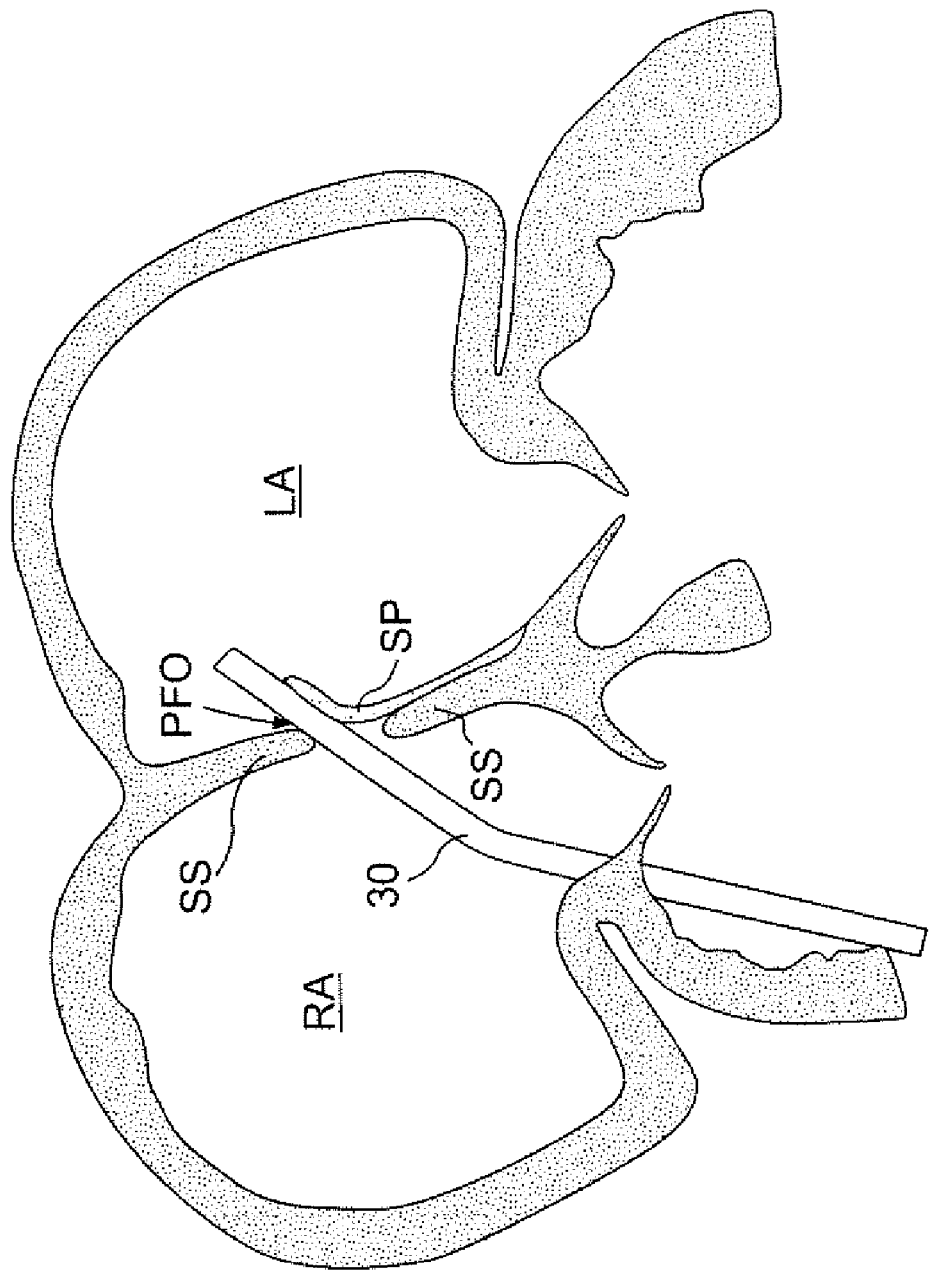
FIG. 3 is a guide catheter inserted through a PFO and into the left atrium, according to an embodiment of the present invention.

FIGS. 3-11 show sequential steps for delivery of closure device 10, according to one aspect of the invention. At the level of the longitudinal section shown in FIG. 3, the inferior vena cava (IVC) is not shown. In an embodiment, a delivery system is passed through the IVC to gain access to the RA and PFO. Other methods of percutaneously, minimally invasively, or more directly obtaining access to the RA and PFO are within the scope of the invention. As embodied herein and shown in FIG. 3, a guide catheter 30 is advanced to and through the PFO track and into the LA. The guide catheter 30 extends across the PFO track, as shown in FIG. 3. The proximal end of the guide catheter 30 includes a hemostasis valve 31. The loading tube 70, the collapsed closure device 10, and delivery catheter 32 are introduced into the guide catheter 30 through the hemostasis valve 31. When fully inserted into the hemostasis valve 31, the distal end of the loading tube 70 abuts the hub (not shown) of the guide catheter 30, preventing the loading tube 70 from continuing to advance down the lumen of the guide catheter 30. The collapsed closure device 10 is then advanced out the loading tube 70 by advancement of the delivery catheter 32 into the lumen of the guide catheter 30. Advancement of the delivery catheter 32 and collapsed closure device 10 continues until the closure device 10 is near the distal end of the guide catheter 30. The loading tube 70 is then withdrawn out of the hemostasis valve 31 and positioned on the delivery catheter 32 towards the proximal end. The hemostasis valve 31 is then closed to stop back bleeding.

Figure 4:
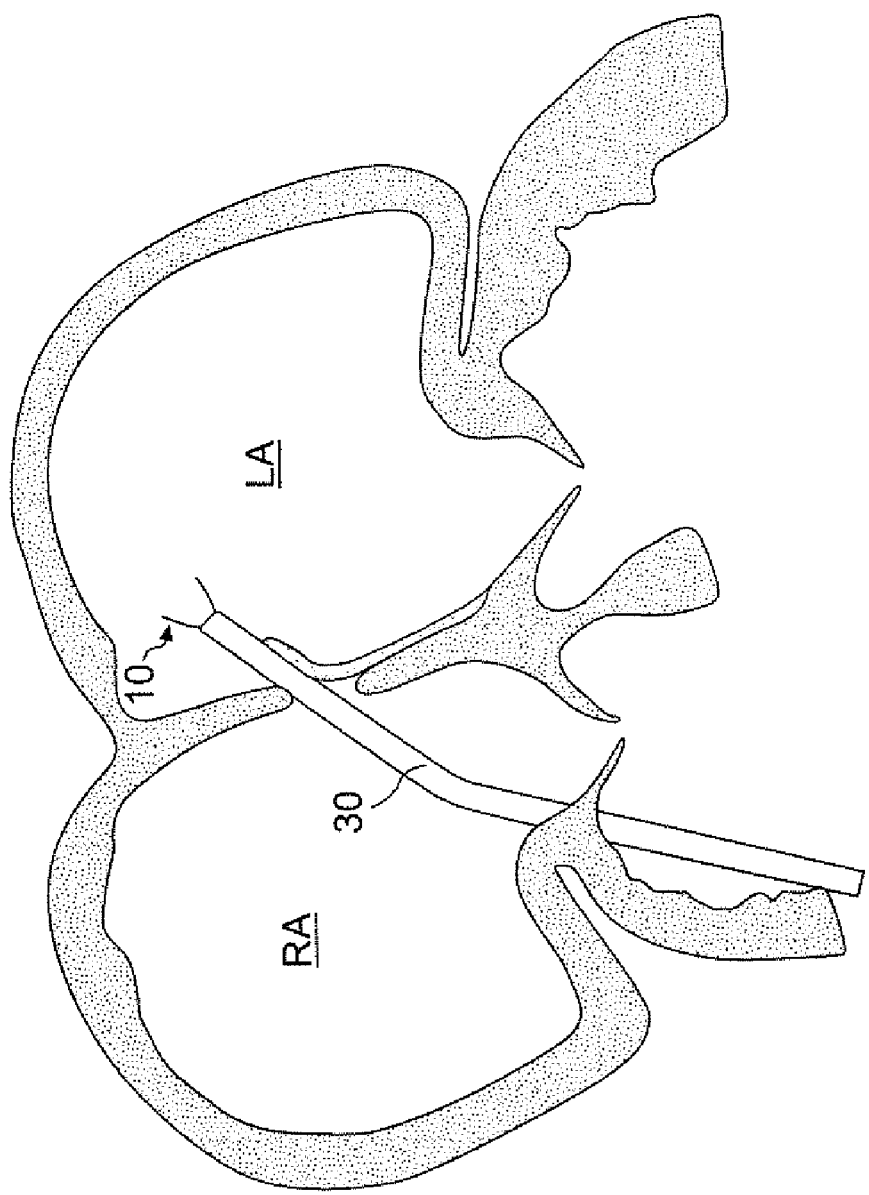
FIG. 4 is a left atrial anchor of the closure device of FIG. 2 being advanced out of the guide catheter, according to an embodiment of the present invention.
Figure 5:
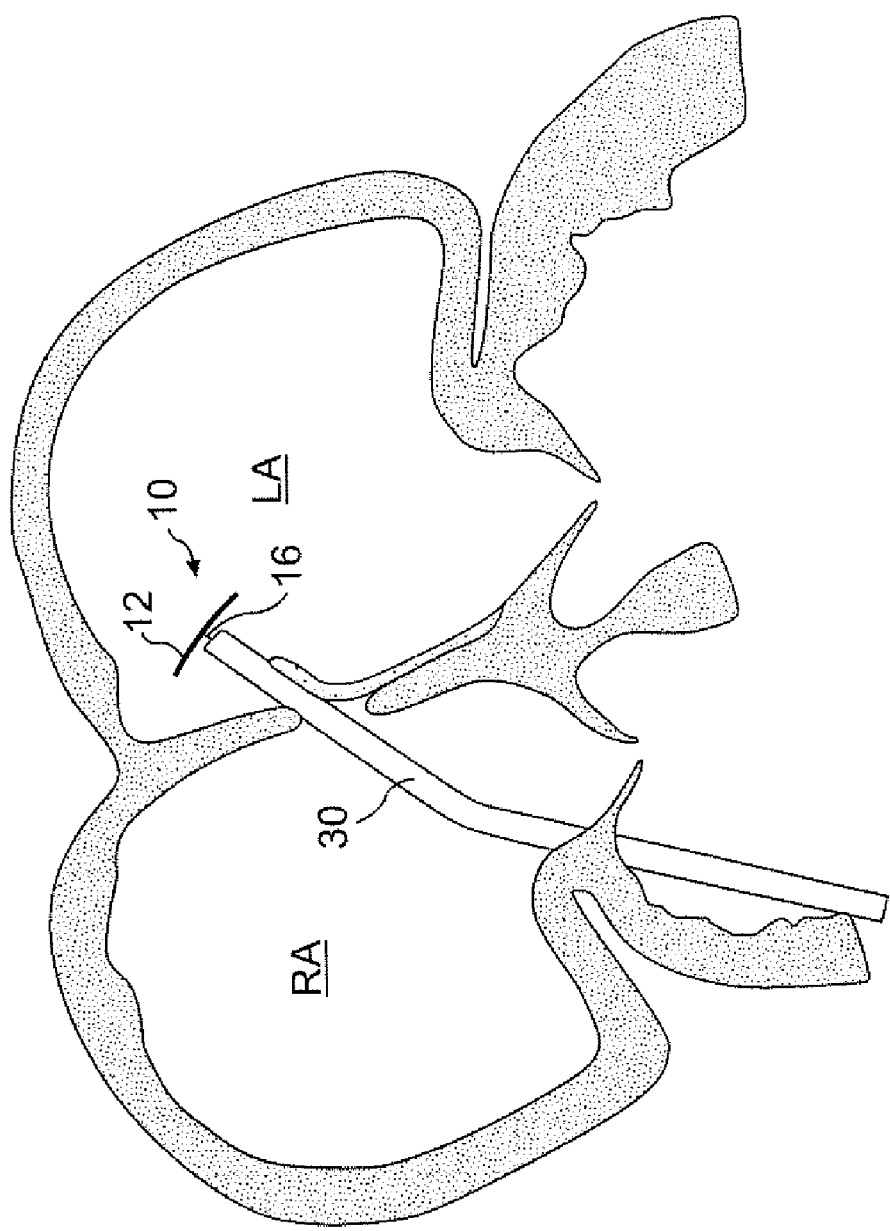
FIG. 5 is the left atrial anchor of the closure device of FIG. 4 advanced out of the guide catheter, according to an embodiment of the present invention.

The delivery catheter 32 is further advanced relative to the guide catheter 30, deploying only the left atrial anchor 12, as shown in FIGS. 4 and 5. FIG. 5 shows the left atrial anchor 12 fully deployed from the guide catheter 30 in the left atrium. Tether 16 extends from anchor 12 into guide catheter 30 and through delivery catheter 32. As discussed above, left atrial anchor 12 and right atrial anchor 14 are preferably self-expanding structures, expanding through a mechanical or thermal shape change, for example. Also at this point, right atrial anchor 14 remains within the delivery assembly in a collapsed state.

Figure 6:
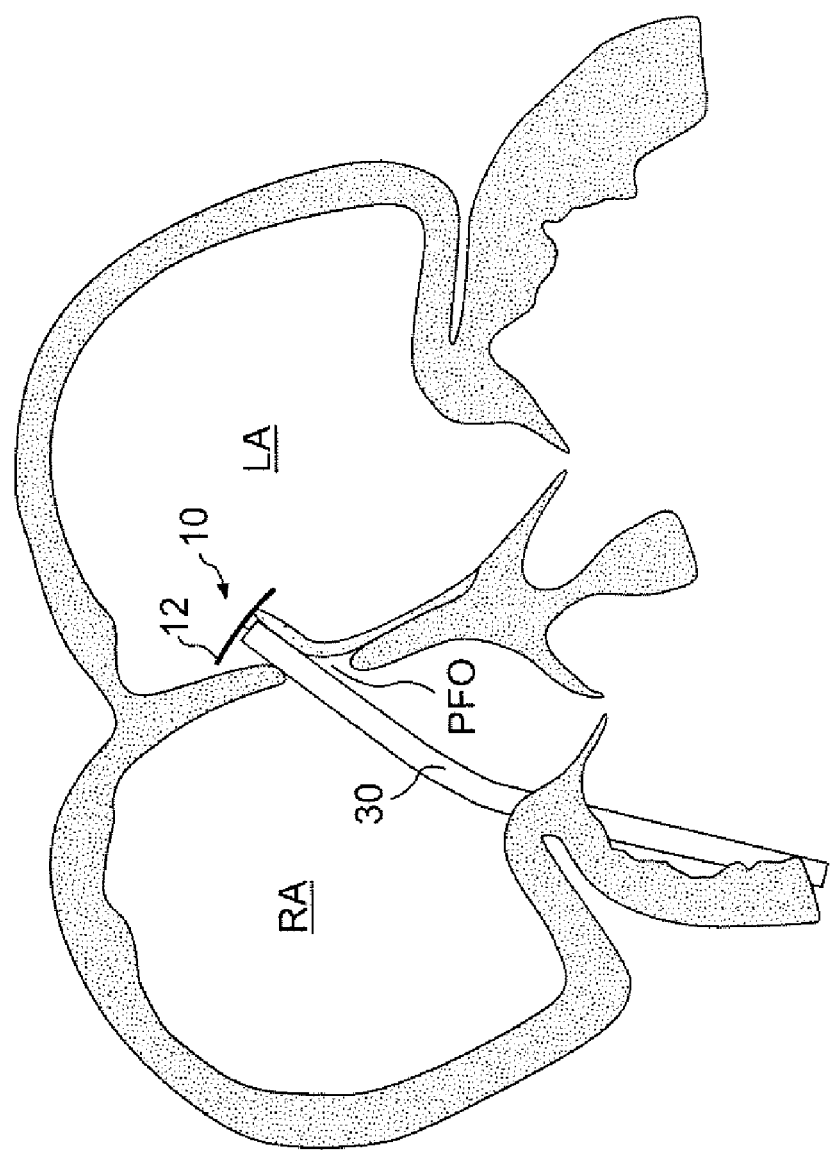
FIG. 6 is the left atrial anchor of FIG. 5 being pulled towards the PFO, according to an embodiment of the present invention.

The delivery catheter 32 and guide catheter 30 are withdrawn, pulling the left atrial anchor 12 against the opening of the PFO track, as shown in FIG. 6. As the tether clip 34 remains in the initial position abutting the proximal end of the delivery catheter 32, the left atrial anchor 12 is pulled against the opening of the PFO track. Next, the tether clip 34 is re-positioned several centimeters proximally on the tether 16.

Figure 7:
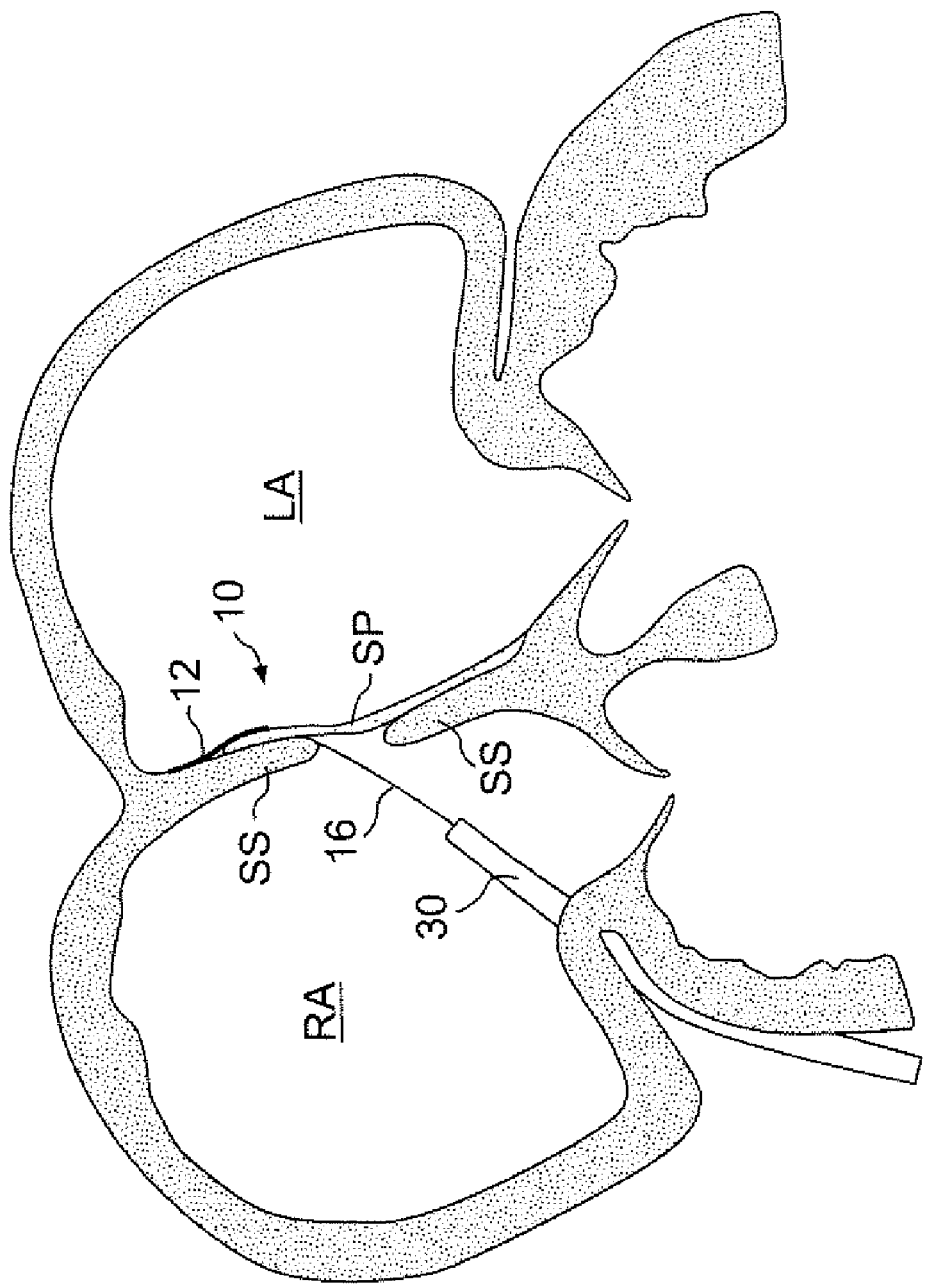
FIG. 7 is the guide catheter pulled proximally into the right atrium and the left atrial anchor seated against a septal wall, according to an embodiment of the present invention.

As shown in FIG. 7, a significant portion of the PFO track (specifically the portion of the track between the superior portion of the septum primum and septum secundum) runs along and roughly parallel with the septal wall. A feature of closure device 10 according to this embodiment is that left atrial anchor 12 and tether 16 are flexibly connected, and tether 16 is itself preferably flexible, to allow tether 16 to extend through the PFO track, while left atrial anchor 12 remains significantly apposed to the left atrial surface. Tether 16 is able to extend from left atrial anchor 12 at an obtuse angle. In many instances, left atrial anchor 12, with tension applied from tether 16, may mechanically close and thereby seal the PFO by bringing the septum primum (SP) into sealing contact with the septum secundum (SS). The effectiveness of this seal can be tested at this time by conventional techniques, such as contrast visualization, or a Valsalva maneuver combined with injection of bubbles, visualized with transesophageal ultrasound or intracardiac ultrasound. If the seal is ineffective, closure device 10 can be removed as described later, and exchanged for a different device. Alternatively, the device 10 can be repositioned as will be described below.

The guide catheter 30 and delivery catheter 32 are further withdrawn relative to the PFO track, until the distal end of the guide catheter 30 is well within the right atrium, as shown in FIG. 7. The right atrial anchor 14, still collapsed within the lumen of the guide catheter 30, moves together with the guide catheter 30 and delivery catheter 32. With the tether clip 34 previously positioned proximally, the catheters 30, 32 and the collapsed right atrial anchor 14 can freely slide proximally relative to the tether 16 and the left atrial anchor 12.

Once left atrial anchor 12 is positioned, right atrial anchor 14 may be deployed. As shown in FIG. 7, initial deployment of right atrial anchor 14 is preferably performed with the delivery catheter and the collapsed right atrial anchor 14 withdrawn sufficiently away from left atrial anchor 12 and the right atrial septal wall, so that right atrial anchor 14 does not impinge on the wall when it initially expands. This also assures that right atrial anchor 14 will not inadvertently deploy in the PFO track or the left atrium. Because right atrial anchor 14 is not permanently attached to tether 16, anchor 14 is free to be positioned in such a location away from the right atrial septal wall.

Figure 8:
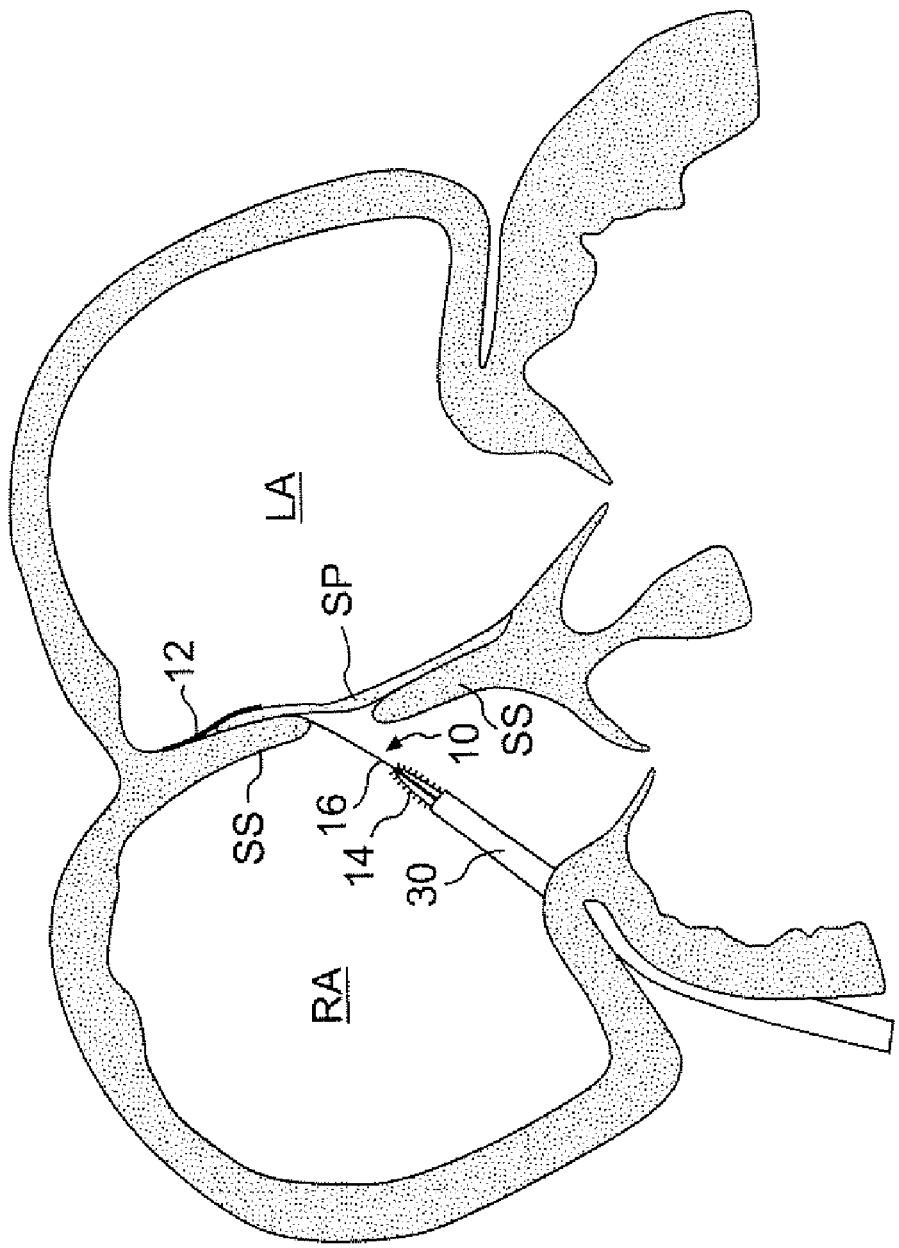
FIG. 8 is a right atrial anchor of the closure device of FIG. 2 being extended from the guide catheter, according to an embodiment of the present invention.
Figure 9:
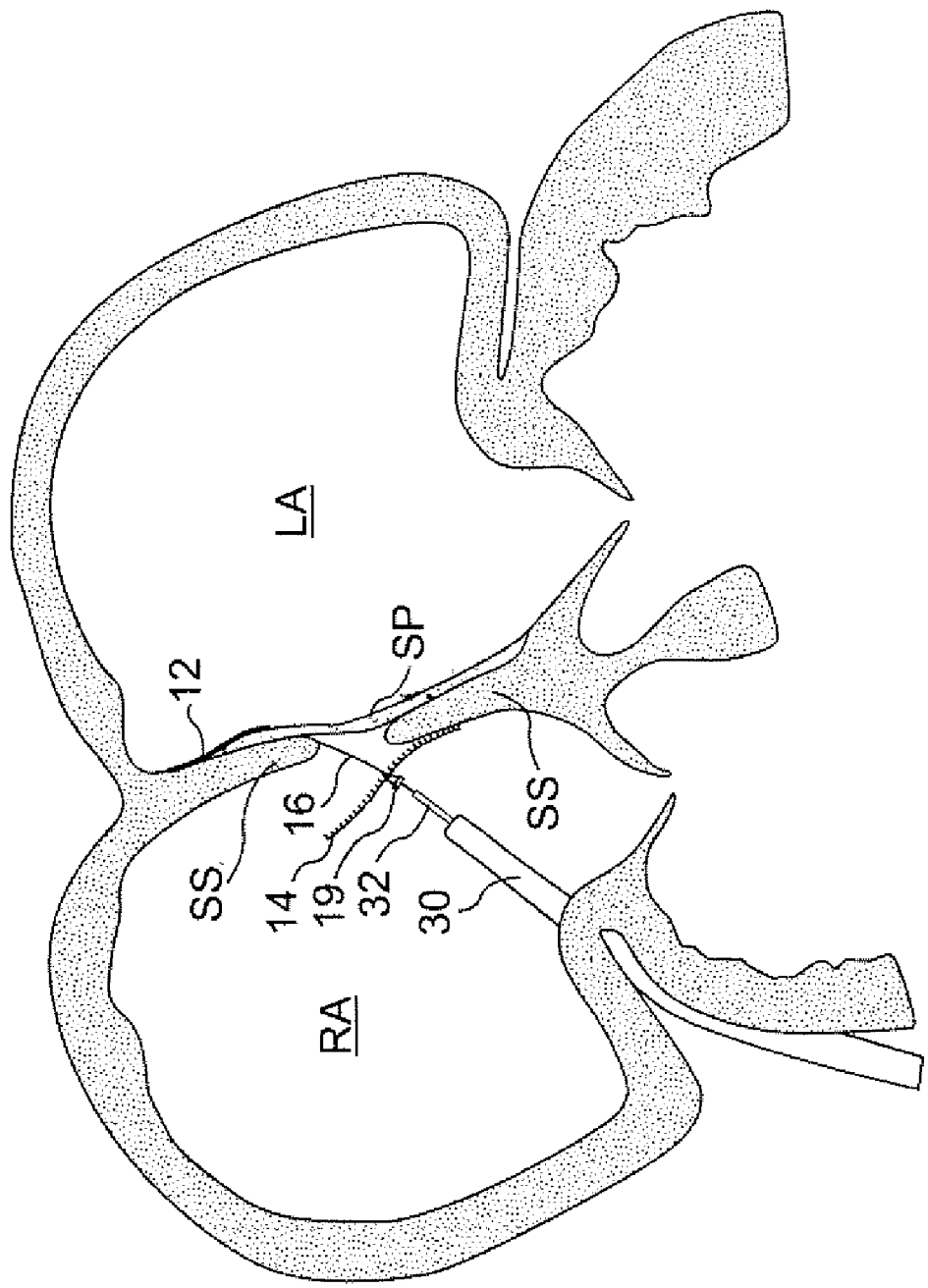
FIG. 9 is the right atrial anchor deployed from the guide catheter, according to an embodiment of the present invention.
Figure 10:
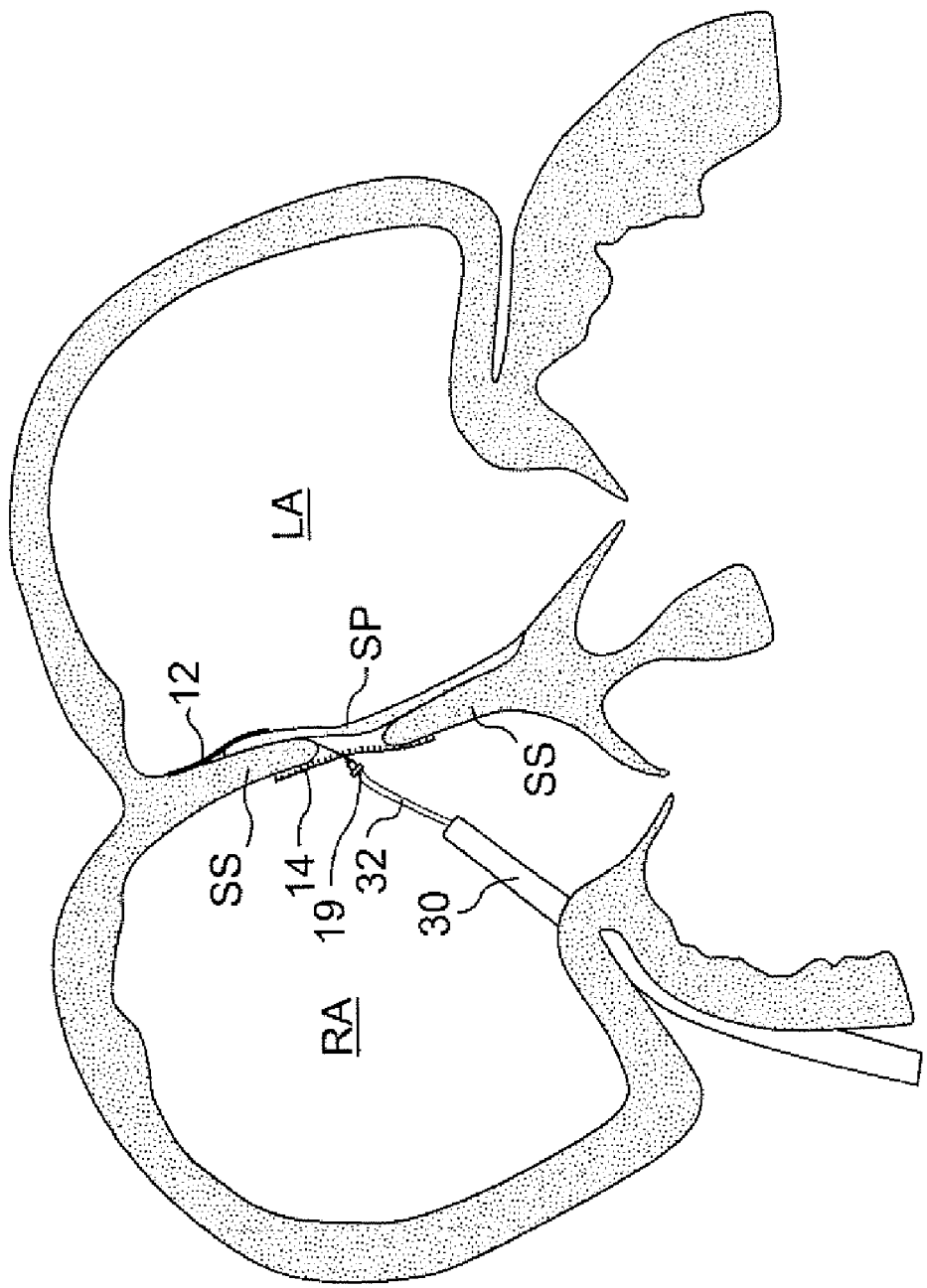
FIG. 10 is the right atrial anchor advanced to contact the septal wall, according to an embodiment of the present invention
Figure 11:
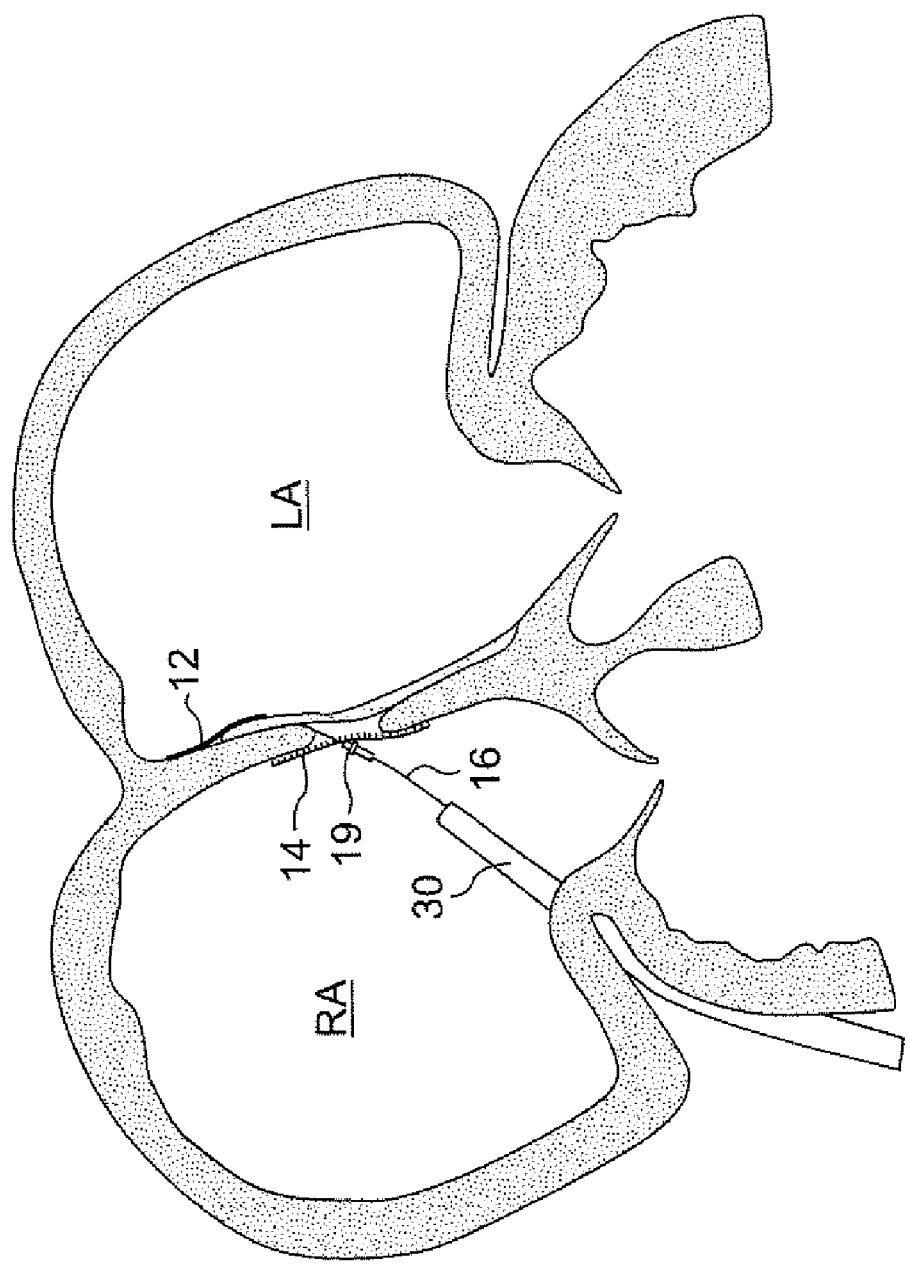
FIG. 11 is the right atrial anchor fixed to a tether of the closure device of FIG. 2, according to an embodiment of the present invention.

With the guide catheter 30 positioned in the right atrium, the right atrial anchor 14 is deployed by advancing the delivery catheter 32 relative to the guide catheter 30, as shown in FIGS. 8-10. This relative movement results in full deployment of right atrial anchor 14 within the right atrium RA, as shown in FIG. 9 At this stage of the delivery method, tether 16 passes through right atrial anchor 14 and preferably extends continuously through delivery catheter 32 and guide catheter 30 to the proximal end of the delivery catheter 32. Light tension is maintained on the tether 16 from the proximal end to prevent slack on the portion of the tether 16 between the left and right atrial anchors 12, 14.

In the next step of this embodiment of a closure device delivery method, right atrial anchor 14 is advanced into contact with the right atrial septal wall, as shown in FIG. 10. This is accomplished by advancing right atrial anchor 14 and delivery catheter 32 along tether 16 until right atrial anchor 14 is in a desired position relative to left atrial anchor 12, the septal wall, and the PFO, and has a desired amount of tension on left atrial anchor 12. It is preferred that left atrial anchor 12 have sufficient tension applied that the septum primum (SP) is brought into sealing apposition with the septum secundum (SS). This apposition, in many cases, may be enough to effectively close and seal the PFO. If desired, at this point in the delivery method, the effectiveness of the closure and seal can again be tested by conventional techniques, such as those described above. If the seal is ineffective, closure device 10 can be removed as described later, and exchanged for a different device (e.g., one of a different size). Alternatively, the device 10 can be repositioned as described later.

The right atrial anchor 14 is advanced until it makes contact with the right atrial end of the PFO track, thus closing it off. The tether clip 34 is then repositioned back to abut the proximal end of the delivery catheter 32 to temporarily maintain the relative positions of the left and right atrial anchors 12, 14. A test of the effectiveness of the closure of the PFO track can then be performed, as described earlier. Note that the distal end of the delivery catheter 32 is not fully connected to the right atrial anchor 14, but is merely abutting it. This arrangement allows for the delivery catheter 32 to pivot relative to the right atrial anchor 14 when abutting the right atrial anchor 14, as shown in FIG. 10. Therefore, the natural orientation that the right atrial anchor 14 takes as it conforms to the wall of the right atrium is not impacted by the orientation of the delivery catheter 32 (or guide catheter 30), enabling the position of the PFO closure device 10 to accurately represent the final state of closure, once the tether is cut and all catheters removed.

Up to this point, the two primary components of the delivery catheter 32, the inner tube 38 and the outer tube 36, have been secured together by way of a touhy-borst fitting 33 in a y-adaptor 35 at the proximal end of the outer tube 36, as shown in FIG. 13. The touhy-borst fitting 33 is initially tightened to prevent relative movement between the inner tube 38 and the outer tube 36. The inner tube 38 initially extends several cm proximally of the touhy-borst fitting 33.

The lock 20, which is initially positioned on the tether 16, several cm proximal of the distal end of the tether 16, is now advanced distally to permanently secure the position of the right atrial anchor 14 relative to the tether 16. To advance the lock 20, the touhy-borst fitting 33 securing the inner tube 38 and the outer tube 36 is loosened. Then, the inner tube 38 is advanced while maintaining the position of the outer tube 36 against the right atrial anchor 14. To prevent creating slack on the tether 16, light tension is applied at its proximal end.

The lock 20 is advanced along the tether 16 under fluoroscopic visualization until it abuts the hub 19 of the right atrial anchor 14. At this point, the delivery catheter 32 is withdrawn several cm, and the PFO closure is re-assessed as discussed previously. In some instances, the right and left atrial anchors 12, 14 may need to be further tightened relative to each other. This can be done by re-advancing the inner tube 38 to the lock 20. The lock 20 is then incrementally advanced along the tether 16, shortening the length of the tether 16 between the left and right atrial anchors 12, 14.

At this point, the effectiveness of the closure and sealing of the PFO can be tested by conventional techniques, such as contrast visualization, or a Valsalva maneuver combined with injection of bubbles, visualized with (TEE) or intracardiac ultrasound.

Figure 22:
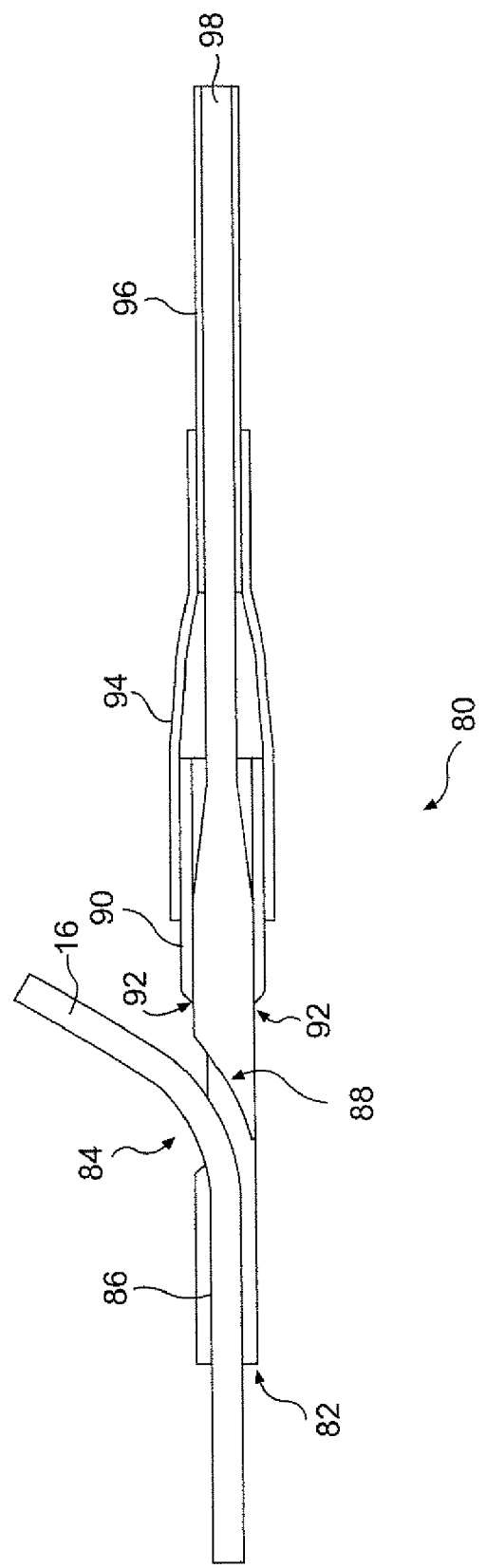
FIG. 22 is a cross-sectional side view of a portion of a cutting tool, according to one aspect of the present invention.

Once a satisfactory closure of the PFO track is confirmed, the tether 16 may be cut at a position near the right atrial anchor 14. A cutting tool 80 is used to perform this step. An embodiment of a cutting tool 80 is illustrated in FIG. 22. The cutting tool 80 includes a tubular cutting element 90, preferably formed of stainless steel, with a sharpened distal edge 92. The cutting element 90 is connected to an outer tube 96 via a linking portion 94. Outer tube 96 extends to the proximal end of the cutting tool 80. The outer tube 96 is preferably incorporates a wire braid (not shown) to impart a relatively high torsional stiffness.

The cutting element 90 surrounds a tether guide 86, preferably formed from metallic hypotubing, with an outer diameter close to the inner diameter of the cutting element 90. The tether guide 86 incorporates a distal opening 82. A lateral opening 84 is a short distance, preferably about 1 mm to about 5 mm proximal of the distal opening 82. The tether guide 86 is secured about the distal end of a central wire 98. The central wire 98, preferably made of stainless steel, extends proximally through the outer tube to the proximal end of the cutting tool 80. The distal portion of the central wire 98 is enlarged to fill the inside diameter of the tether guide 86. The distal end of the central wire 98 further incorporates a bevel 88. Central wire 98 moves axially and rotationally relative to outer tube 96. At the proximal end of the cutting tool (not shown) is a handle mechanism, which facilitates controlled relative rotation and longitudinal movement between the central wire 98 and the outer tube 96.

The initial position of the cutting element 90 is just proximal to the lateral opening 84 in the tether guide 86, as shown in FIG. 22. The handle mechanism when activated causes the outer tube 96 and cutting element 90 to rotate relative to the central wire 98 and the tether guide 86. A screw or other suitable mechanism in the handle mechanism further causes the outer tube 96 and cutting element 90 to advance distally along the tether guide 86, until the cutting element 90 is just distal of the lateral opening 84 thereby severing tether 16.

In use, the cutting tool 80 is loaded over the proximal end of the tether 16, as shown in FIG. 22, the tether 16 being inserted in the distal opening 82 of the tether guide 86. The bevel 88 causes the tether 16 to emerge out the lateral opening 84. The cutting tool 80 is advanced along the tether 16 until the distal end of the cutting tool 80 abuts the lock 20. At this point, the handle mechanism is activated, which causes the cutting element 90 to advance and slice the tether 16. The PFO closure device 10 is now fully implanted.

There are several points during the delivery of closure device 10 where device 10 can be completely removed from the patient. This may be necessary if, for example, device 10 is not creating a complete seal due to any of a number of causes, including, for example, the selected device being too small.

For example, after deployment of the left atrial arm 12, but before deployment of the right atrial arm 14 (the position shown in FIG. 7), the deployed left atrial arm 12 can be captured by advancement of the guide catheter 30 relative to the tether 16 and left atrial anchor 12, which are fixed relative to the PFO track. The guide catheter 30 is advanced through the PFO track until it meets the left atrial anchor 12. The guide catheter 30 continues to advance, causing the left atrial anchor 12 to essentially resume the position it was in prior to initial deployment. Light tension is applied to the tether 16 during the advancement.

Alternatively, the device 10 may be retrieved after deployment of the right atrial anchor 14, but before advancement of the lock 20 (the position shown in FIG. 10). The deployed right atrial anchor 14 can be captured by use of a snare catheter (not shown). A preferred snare catheter is commercially available by Microvena (ev3), and sold under the trade name Amplatz Gooseneck Snare. The outer tube 36 of delivery catheter 32 is left in place abutting the right atrial anchor 14. The tether clip 34, y-adaptor, and the inner tube 38 of delivery catheter 32 are all removed from the tether in a proximal direction, leaving the outer tube 36 of delivery catheter 32 in place. The snare is advanced over the proximal end of the outer tube 36 of delivery catheter 32 and along the annular space between the guide catheter 30 and the outer tube 36 of delivery catheter 32. The snare is activated to engage the enlarged ring 19a on the hub 19 of the right atrial anchor 14. Then the snare, together with the outer tube 36 of delivery catheter 32, is withdrawn relative to the guide catheter 30 and tether 16. Continued proximal movement of the snare causes the right atrial anchor 14 to collapse into the guide catheter 30. Once the collapsed right atrial anchor is near the hemostasis valve 31 of the guide catheter 30, the loading tube 70 is re-advanced through the hemostasis valve 31. The collapsed right atrial anchor 14 is drawn into the loading tube 70, allowing the right atrial anchor 14, outer tube 36 of delivery catheter 32, and snare to be removed from the guide catheter 30. The left atrial anchor 12 then may be removed by advancing the guide catheter 30 through the PFO track, while maintaining tension on the tether 16. Once the guide catheter 30 contacts the left atrial anchor 12, continued advancement of the guide catheter 30 relative to the left atrial anchor 12 will cause it to collapse into the guide catheter 30, allowing subsequent removal.

The various described embodiments of closure devices and methods and tools for their delivery are suitable for closure of a wide variety of PFOs. For example, PFOs with a relatively long overlap between the septum primum (SP) and septum secundum (SS) may be suitably closed, as shown in FIG. 2.

Other embodiments of the invention will be apparent to those skilled in the art from consideration of the specification and practice of the invention disclosed herein. The specification and examples are exemplary, with a true scope and spirit of the invention being indicated by the following claims.

The invention claimed is:

1. A device for sealing a passageway in a human body, the device comprising:
   a first anchor adapted to be placed proximate a first end of the passageway, the first anchor including a central hub and a plurality of first loop structures, each first loop structure having a first end connected to the central hub and a second free end, and each first loop structure including an outer loop portion and a flexible line for maintaining a connection between the first loop structure and the central hub in case of fracture of the outer loop portion;
   a second anchor adapted to be placed proximate a second end of the passageway; and
   an elongate member adapted to extend through the passageway and connect the first and second anchors, the elongate member having a first end fixedly connected to one of the first and second anchors.

2. The device of claim 1, wherein the passageway is a patent foramen ovale.

3. The device of claim 1, wherein the loop structures of the first anchor form first anchor arms.

4. The device of claim 3, wherein the first anchor arms can assume a collapsed state and a deployed state.

5. The device of claim 1, wherein the elongate member is flexible.

6. The device of claim 1, wherein the second anchor includes a plurality of second loop structures.

7. The device of claim 6, wherein the loop structures of the second anchor form second anchor arms.

8. The device of claim 7, wherein the second anchor arms extend from a central hub of the second anchor.

9. The device of claim 8, wherein the second anchor includes a covering that spans the arms.

10. The device of claim 6, wherein each second loop structure includes a marker.

11. The device of claim 6, wherein each of the second loop structures has a first end connected to the second anchor and a second free end.

12. The device of claim 6, wherein at least a portion of each of the plurality of second loop structures is movable independently from the other second loop structures.

13. The device of claim 6, wherein each of the second loop structures is a planar loop.

14. The device of claim 6, wherein each second loop structure includes an outer loop portion and means for maintaining a connection between the second loop structure and a central hub of the second anchor in case of fracture of the outer loop portion of the second loop structure.

15. The device of claim 1, further comprising a lock.

16. The device of claim 15, wherein the lock includes a tube that is movable only in a distal direction along the elongate member.

17. The device of claim 1, further comprising means for preventing proximal movement of the second anchor with respect to the elongate member.

18. The device of claim 1, wherein the flexible line passes through a hole in at least one of the first loop structures.

19. The device of claim 18, wherein the flexible line passes through the first end of the elongate member fixedly connected to the first anchor.

20. The device of claim 1, wherein the first anchor is pivotable relative to the elongate member.

21. The device of claim 1, wherein the second anchor is pivotable relative to the elongate member.

22. The device of claim 1, wherein the first end of the elongate member is fixedly connected to the first anchor.

23. The device of claim 1, wherein each first loop structure includes a marker.

24. The device of claim 1, wherein at least a portion of each of the plurality of first loop structures is movable independently from the other first loop structures.

25. The device of claim 1, wherein each of the first loop structures is a planar loop.

26. The device of claim 1, wherein the flexible line maintains the connection between a plurality of first loop structures and the central hub.

27. The device of claim 1, wherein a separate flexible line maintains the connection between each first loop structure and the central hub.

28. An assembly for sealing a passageway in a heart, the assembly comprising: a guide catheter capable of extending to the passageway; and a closure device capable of sealing the passageway, the closure device including a first anchor adapted to be placed proximate a first end of the passageway, the first anchor including a central hub and a plurality of first loop structures, each first loop structure having a first end connected to the central hub and a second free end, and each first loop structure including an outer loop portion and a flexible line for maintaining a connection between the outer loop portion and the central hub during fracture of the outer loop portion, a second anchor adapted to be placed proximate a second end of the passageway, and a flexible elongate member adapted to extend through the passageway and connect the first and second anchors, wherein the closure device is positionable within the guide catheter in a first collapsed state and extendable from the guide catheter in a second deployed state.

29. The assembly of claim 28, further comprising a delivery catheter capable of extending to the passageway, and wherein the delivery catheter is extendable through the guide catheter.

30. The assembly of claim 29, wherein the closure device further comprises a lock for preventing proximal movement of the second anchor.

31. The assembly of claim 30, wherein the lock is engagable by the delivery catheter to move the lock along the elongate member to a position adjacent the second anchor.

32. The assembly of claim 28, wherein the passageway is a patent foramen ovale.

33. The assembly of claim 28, further comprising a loading tube.

34. The assembly of claim 33, wherein the closure device is positionable within the loading tube in its first collapsed state.

35. The assembly of claim 28, wherein each of the first loop structures is planar.

36. The assembly of claim 28, wherein the flexible line passes through a hole in at least one of the first loop structures.

37. The assembly of claim 36, wherein the flexible elongate member has a first end fixedly connected to the first anchor, the flexible line passing through the first end of the elongate member.

38. The assembly of claim 28, wherein the flexible line maintains the connection between a plurality of the first loop structures and the central hub.

39. The assembly of claim 28, wherein a separate flexible line maintains the connection between each first loop structure and the central hub.

40. The assembly of claim 28, wherein the second anchor includes a plurality of second loop structures.

41. The assembly of claim 40, wherein each of the plurality of second loop structures includes an outer loop portion and means for maintaining a connection between the second loop structure and a central hub of the second anchor in case of fracture of the outer loop portion of the second loop structure.

42. A device for sealing a passageway in a human body, the device comprising:
a first anchor adapted to be placed proximate a first end of the passageway, the first anchor including a central hub and a plurality of first loop structures, each first loop structure having a first end connected to the central hub and a second free end, and each first loop structure including an outer loop portion and a web portion for maintaining a connection between the first loop structure and the central hub in case of fracture of the outer loop portion, wherein the web portion includes at least one radial strut and at least one cross strut;
a second anchor adapted to be placed proximate a second end of the passageway; and
an elongate member adapted to extend through the passageway and connect the first and second anchors, the elongate member having a first end fixedly connected to one of the first and second anchors.

43. The device of claim 42, wherein the web portion is thinner than the outer loop portion.

44. An assembly for sealing a passageway in a heart, the assembly comprising: a guide catheter capable of extending to the passageway; and a closure device capable of sealing the passageway, the closure device including a first anchor adapted to be placed proximate a first end of the passageway, a second anchor adapted to be placed proximate a second end of the passageway, and a flexible elongate member adapted to extend through the passageway and connect the first and second anchors, the first anchor including a central hub and a plurality of first loop structures, each first loop structure having a first end connected to the central hub and a second free end, and each first loop structure including an outer loop portion and a web portion for maintaining a connection between the outer loop portion and the first anchor during fracture of the outer loop portion, wherein the web portion includes at least one radial strut and at least one cross strut, wherein the closure device is positionable within the guide catheter in a first collapsed state and extendable from the guide catheter in a second deployed state.

45. The assembly of claim 44, wherein the outer loop portion has a thickness greater than a thickness of the web portion.

* * * * *